United States Patent [19]

Hively et al.

[11] Patent Number: 5,857,978
[45] Date of Patent: Jan. 12, 1999

[54] EPILEPTIC SEIZURE PREDICTION BY NON-LINEAR METHODS

[75] Inventors: Lee M. Hively; Ned E. Clapp; C. Stuart Daw; William F. Lawkins, all of Knoxville, Tenn.

[73] Assignee: Lockheed Martin Energy Systems, Inc., Oak Ridge, Tenn.

[21] Appl. No.: 619,030

[22] Filed: Mar. 20, 1996

[51] Int. Cl.[6] .................................................. A61B 5/04
[52] U.S. Cl. ............................................................ 600/544
[58] Field of Search .................................. 128/731–733; 600/544–546

[56] References Cited

U.S. PATENT DOCUMENTS

| | | | |
|---|---|---|---|
| 5,311,876 | 5/1994 | Olsen et al. ............................. | 128/731 |
| 5,349,962 | 9/1994 | Lockard et al. ........................ | 128/732 |
| 5,392,788 | 2/1995 | Hudspeth ................................ | 128/731 |
| 5,630,425 | 5/1997 | Panescu et al. ....................... | 128/731 X |

OTHER PUBLICATIONS

A. Babloyantz and A. Destexhe, "Low–Dimensional Chaos in an Instance of Epilepsy," *Proc. Natl. Acad. Sci. USA* 83, 3513–3517 (1986).

D.F. Elliott and K. R. Rao, *Fast Transforms, Analyses, Applications,* Academic Press, 1982.

A. M. Fraser and H. L. Swinney, "Independent Coordinates for Strange Attractors from Mutual Information," *Phys. Rev A* 33, 1134–1140 (1986).

J. Glanz, "Do Chaos–Control Techniques Offer Hope for Epilepsy?" *Science* 265, 1174 (1994).

J. Gotman, "Seizure Recognition and Analysis," *Long–term Monitoring in Epilepsy (EEG Suppl. No. 37)*, pp. 133–145 (1985).

G. A. Korn and T. M. Korn, *Mathematical Handbook for Scientists and Engineers,* McGraw–Hill Book Company, New York, 1968.

D. E. Olsen, J. A. Cristion, and C. W. Spaur, "Automatic Detection of Epileptic Seizures Using Electroencephalographic Signals," *Johns Hopkins APL Techn. Digest 12,* 182–191 (1991).

J.P.M. Pijn, "Quantitative Evaluation of EEG Signals in Epilepsy—Nonlinear Associations, Time Delays, and Nonlinear Dynamics," Ph.D. Thesis, University of Amsterdam, 1990.

L. R. Rabiner and B. Gold, *Theory and Application of Digital Signal Processing,* Prentice Hall Inc., 1975.

S.M. Selby and B. Girling, *Standard Mathematical Tables,* p. 390, The Chemical Rubber Co. (14th edition, 1965).

S. J. Schiff, K. Jerger, D. H. Duong, T. Chang, M. L. Spano, and W.L. Ditto, "Controlling Chaos in the Brain," *Nature* 370, 615–620 (1994).

J. C. Schouten, F. Takens, and C. M. van den Bleek, "Maximum–Likelihood Estimation of the Entropy of an Attractor," *Phys. Rev. E* 49, 126–129 (1994).

J. C. Schouten, F. Takens, and C. M. van den Bleek, "Estimation of the Dimension of a Noisy Attractor," *Phys. Rev. E* 50, 1851–1861 (1994).

F. Takens, "On the Numerical Determination of the Dimension of an Attractor," in *Dynamical Systems and Bifurcations,* ed. B.L.J. Braaksma, H.W. Broer, and F. Takens, *Lecture Notes in Mathematics* 1125, 99–106 (1984) Springer– Verlag, Berlin.

(List continued on next page.)

*Primary Examiner*—Jennifer Bahr
*Assistant Examiner*—Ryan Carter
*Attorney, Agent, or Firm*—J. Kenneth Davis

[57] ABSTRACT

Methods and apparatus for automatically predicting epileptic seizures monitor and analyze brain wave (EEG or MEG) signals. Steps include: acquiring the brain wave data from the patient; digitizing the data; obtaining nonlinear measures of the data via chaotic time series analysis tools; obtaining time serial trends in the nonlinear measures; comparison of the trend to known seizure predictors; and providing notification that a seizure is forthcoming.

14 Claims, 19 Drawing Sheets

OTHER PUBLICATIONS

F. J. Taylor, *Digital Filter Design Handbook,* Marcel Dekker, Inc., Publ., New York and Basel, 1983.

J. Theiler, "On the Evidence for Low–Dimensional Chaos in an Epileptic Electroencephalogram," *Phys. Lett. A* 196, 335–341 (1995).

R. C. Watt and S. R. Hameroff, "Phase Space Analysis of Human EEG during General Anesthesia," *Ann. N.Y. Acad. Sci.* 504, 286–288 (1987).

T. Elbert, W. J. Ray, Z. J. Kowalik, J. E. Skinner, K. E. Graf, N. Birbaumer, "Chaos and Physiology: Deterministic Chaos in Excitable Cell Assemblies," Physiological Reviews 74 (1994) 1–47.

S. Blanco, R. Quian Quiroga, O. A. Rosso, and S. Kochen, "Time–frequency analysis of electroencephalogram series," *Physical Review E,* The American Physical Society, vol. 51, No. 3, Mar. 1995.

Weiming Yang and Mingzhou Ding, "Preserving Chaos; Contrl strategies to preserve complex dynamics with potential relevance to biological disorders," *Review E,* The American Physical Society, vol. 51, No. 1 Jan. 1995.

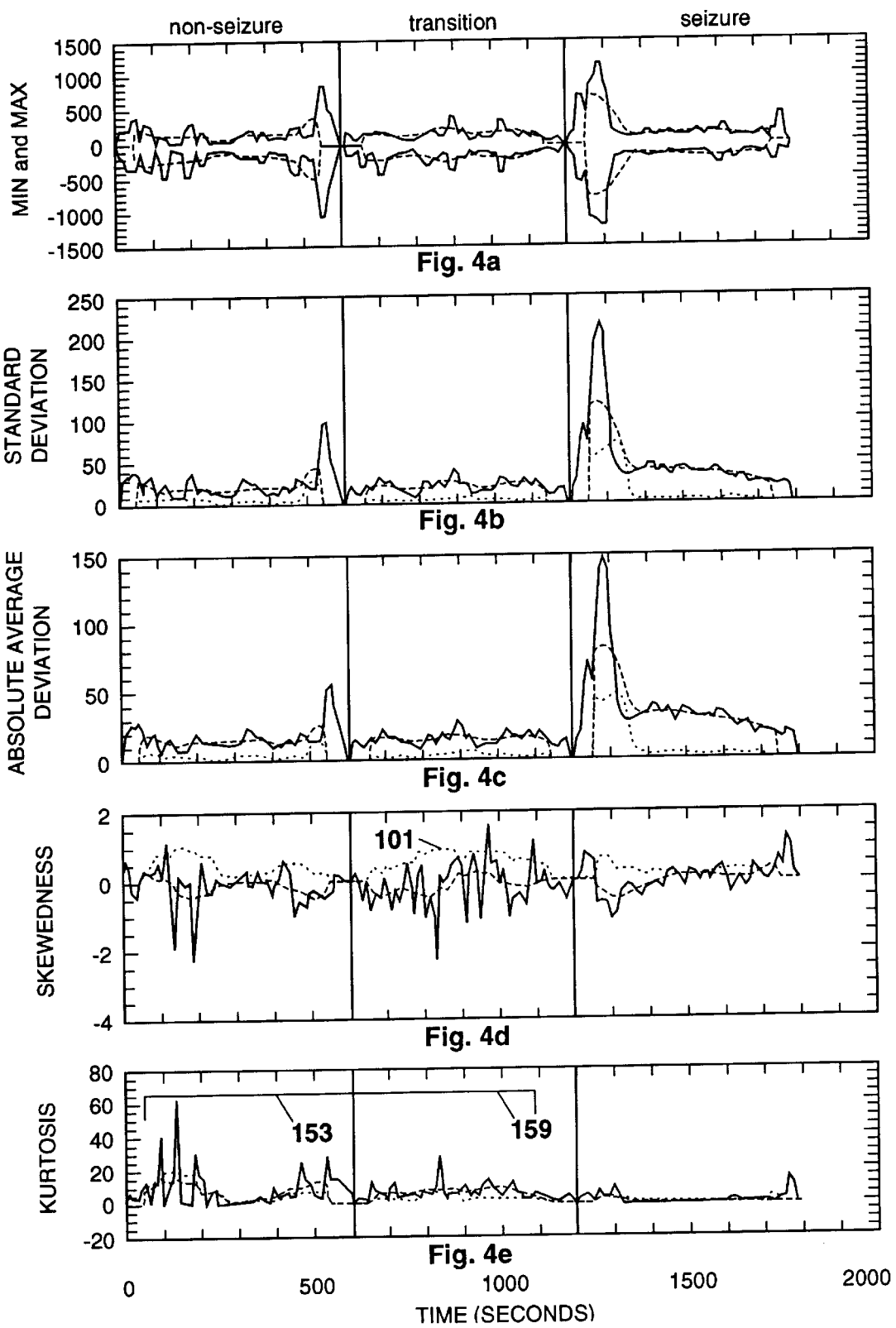

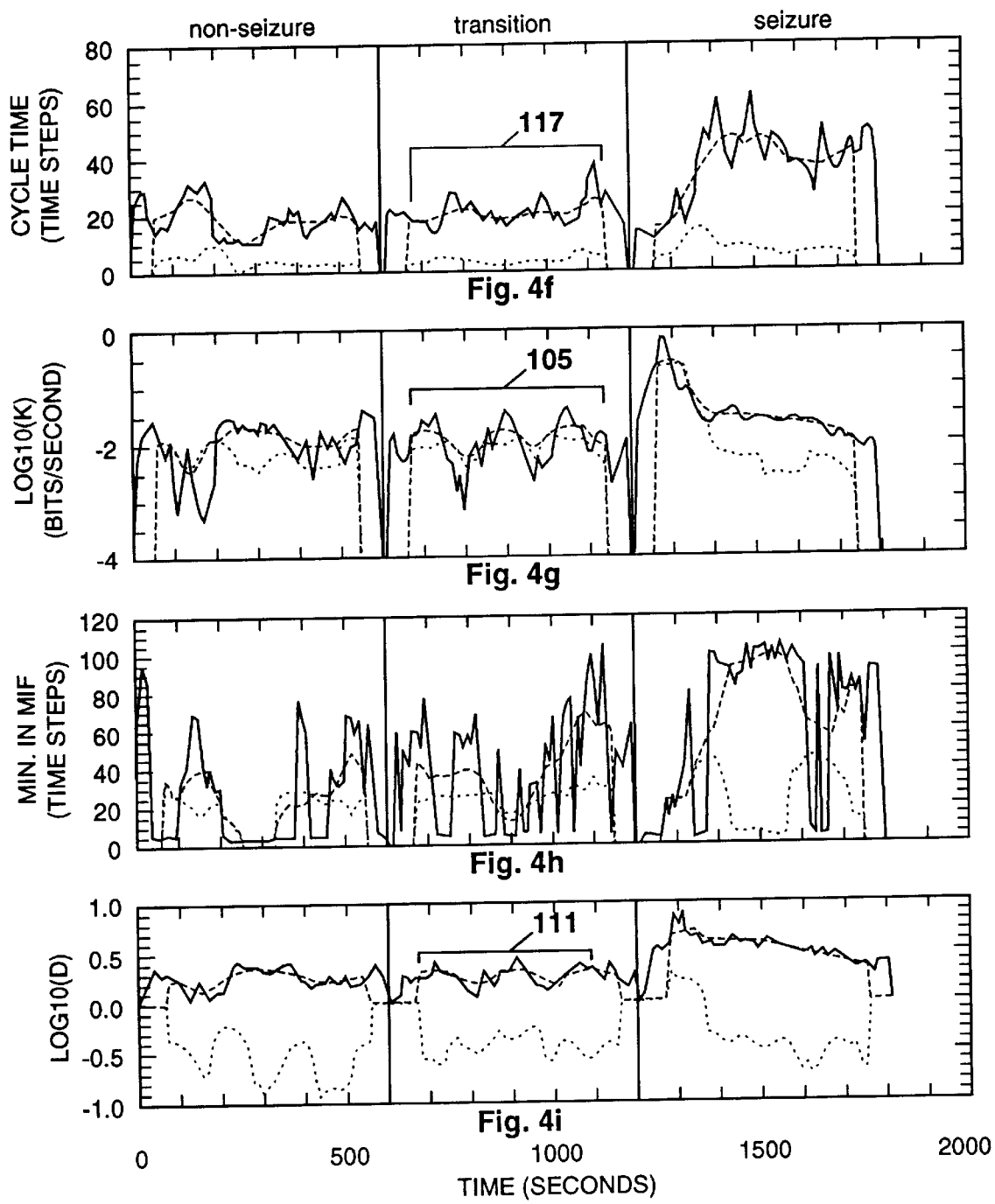

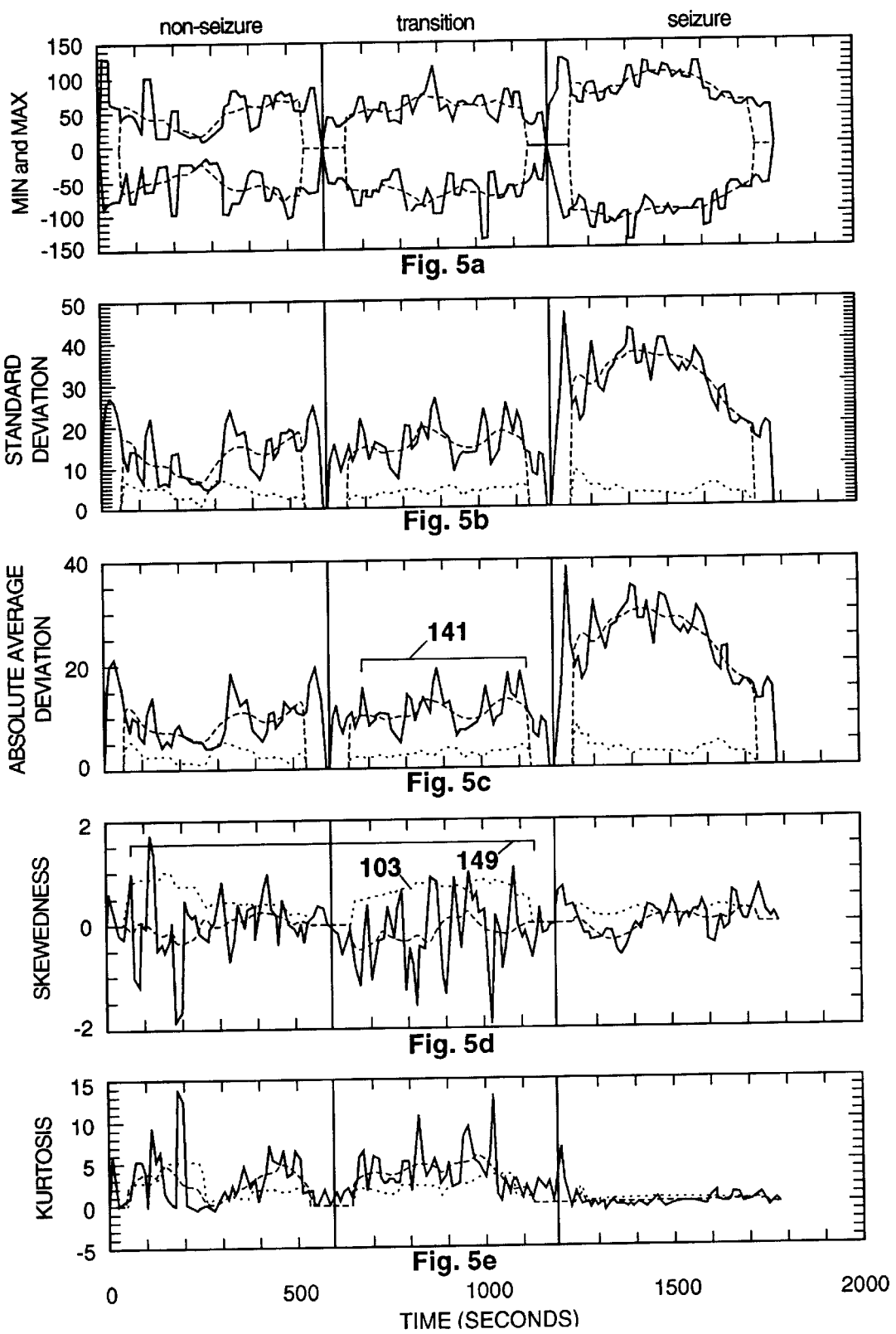

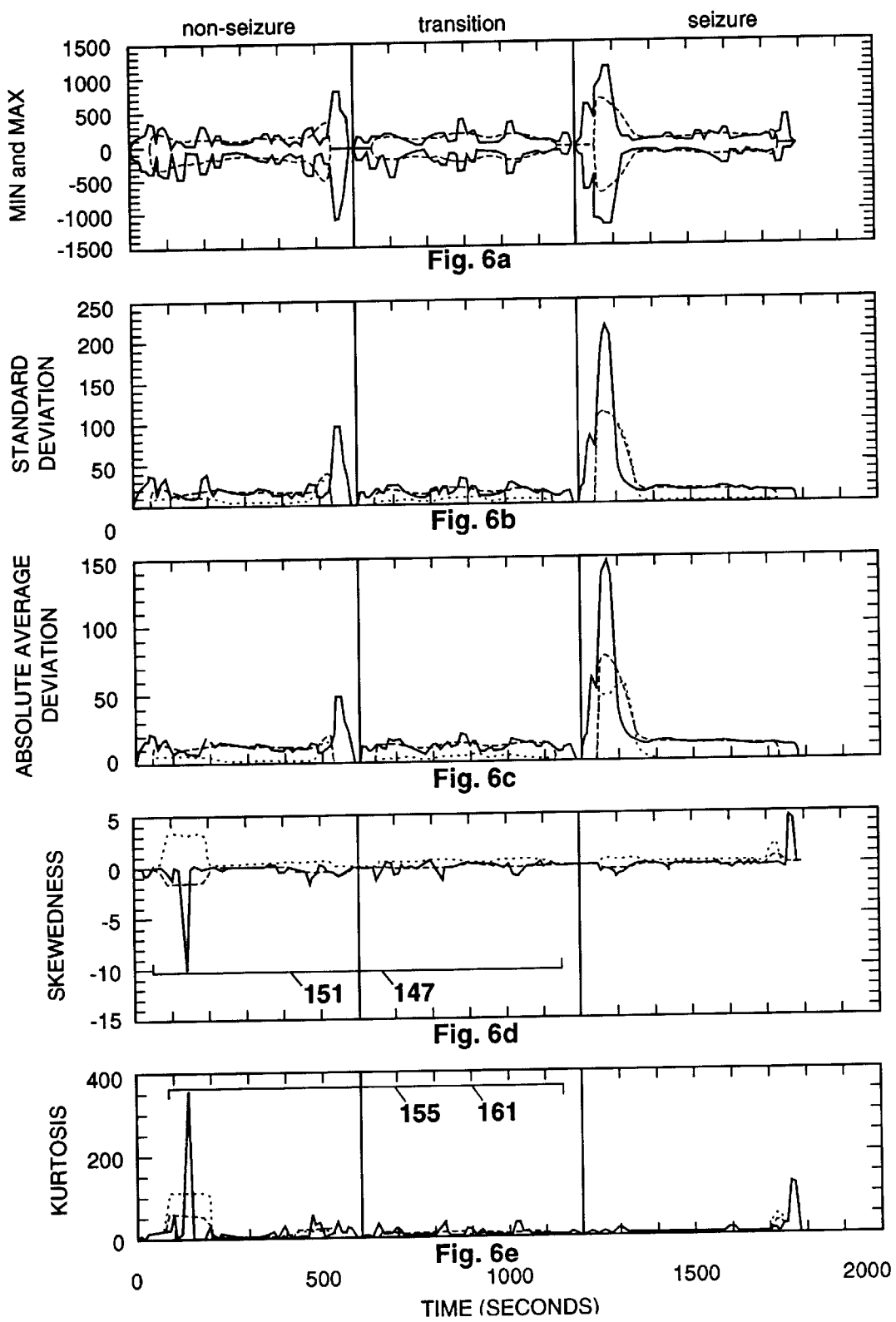

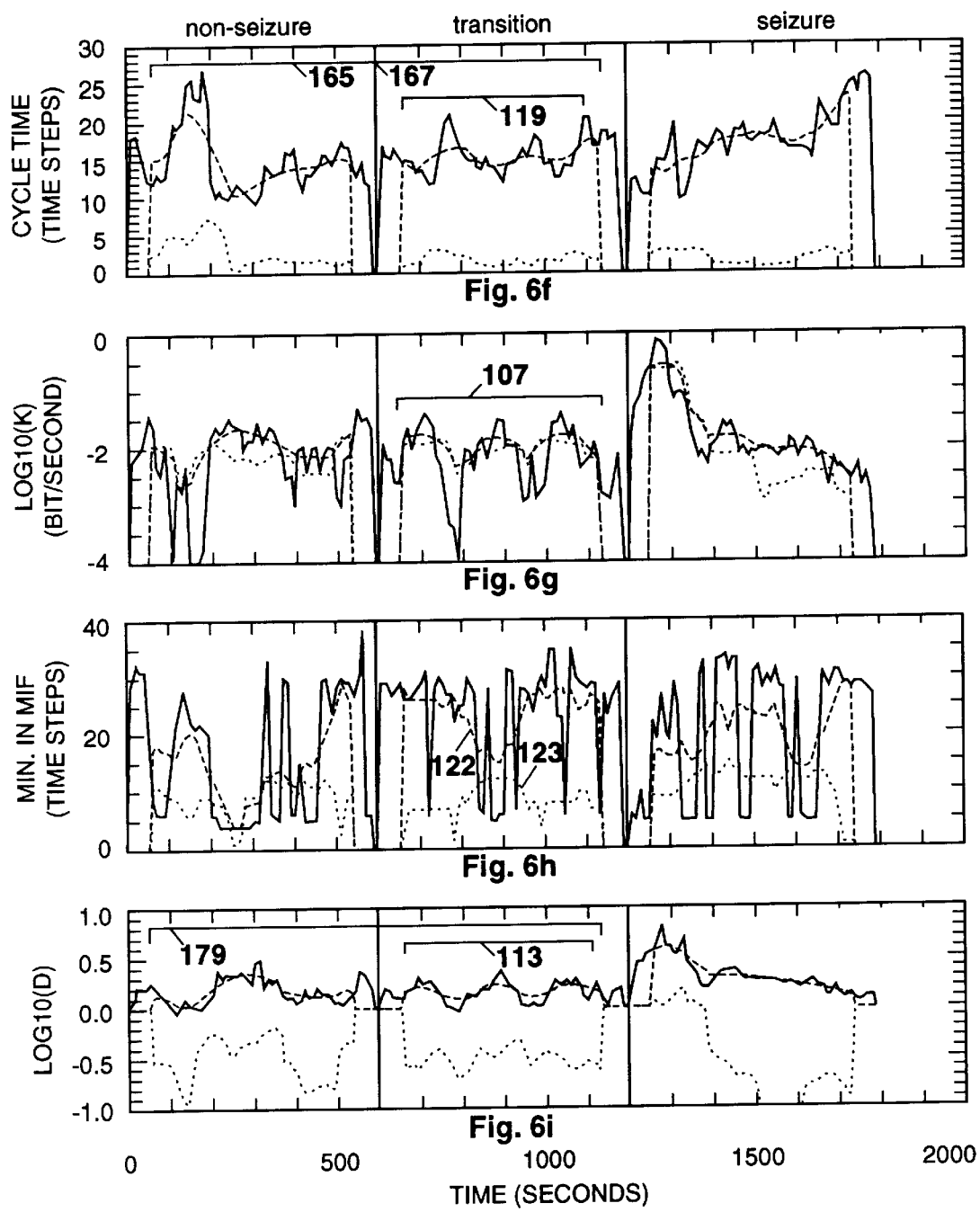

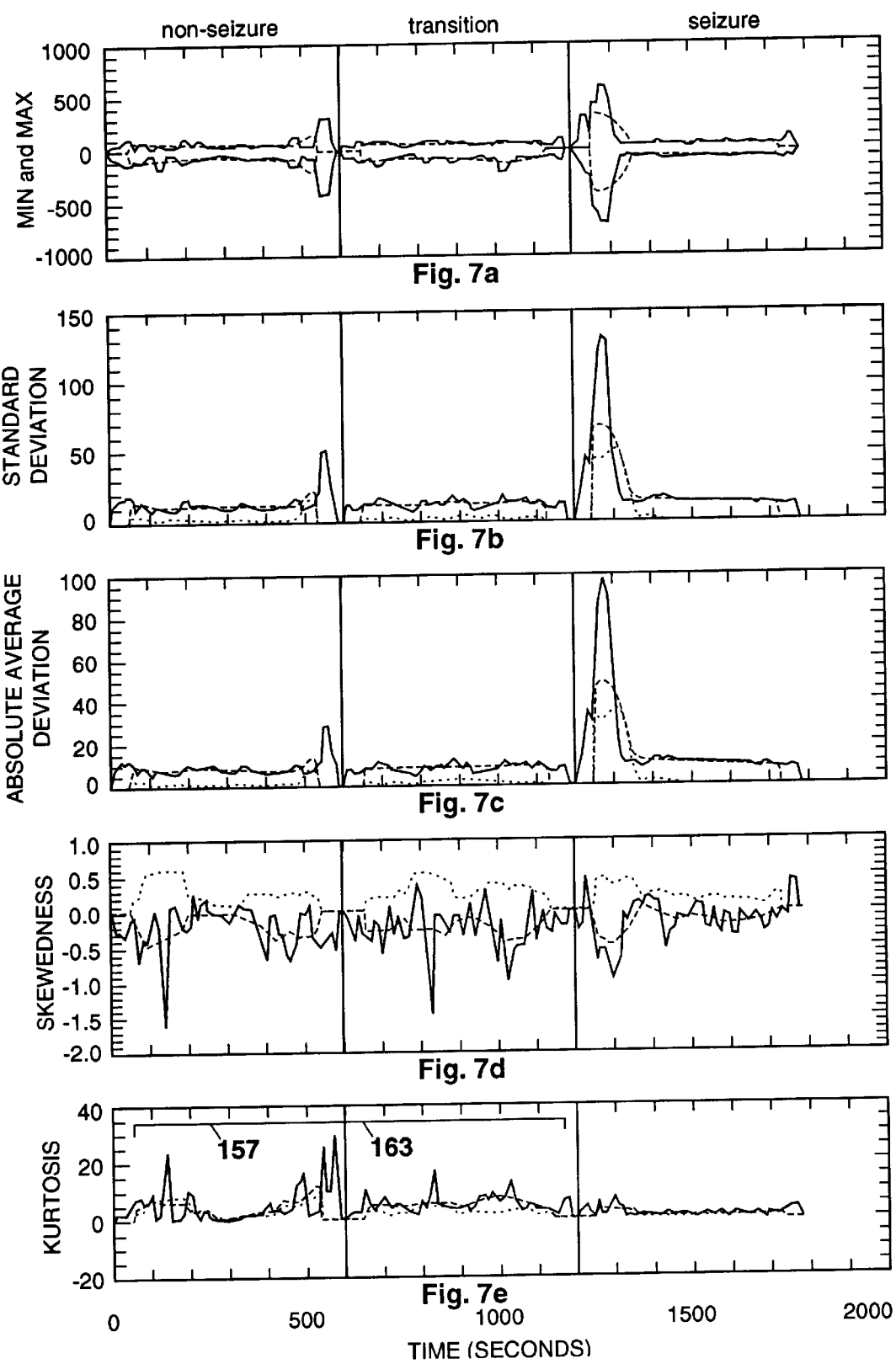

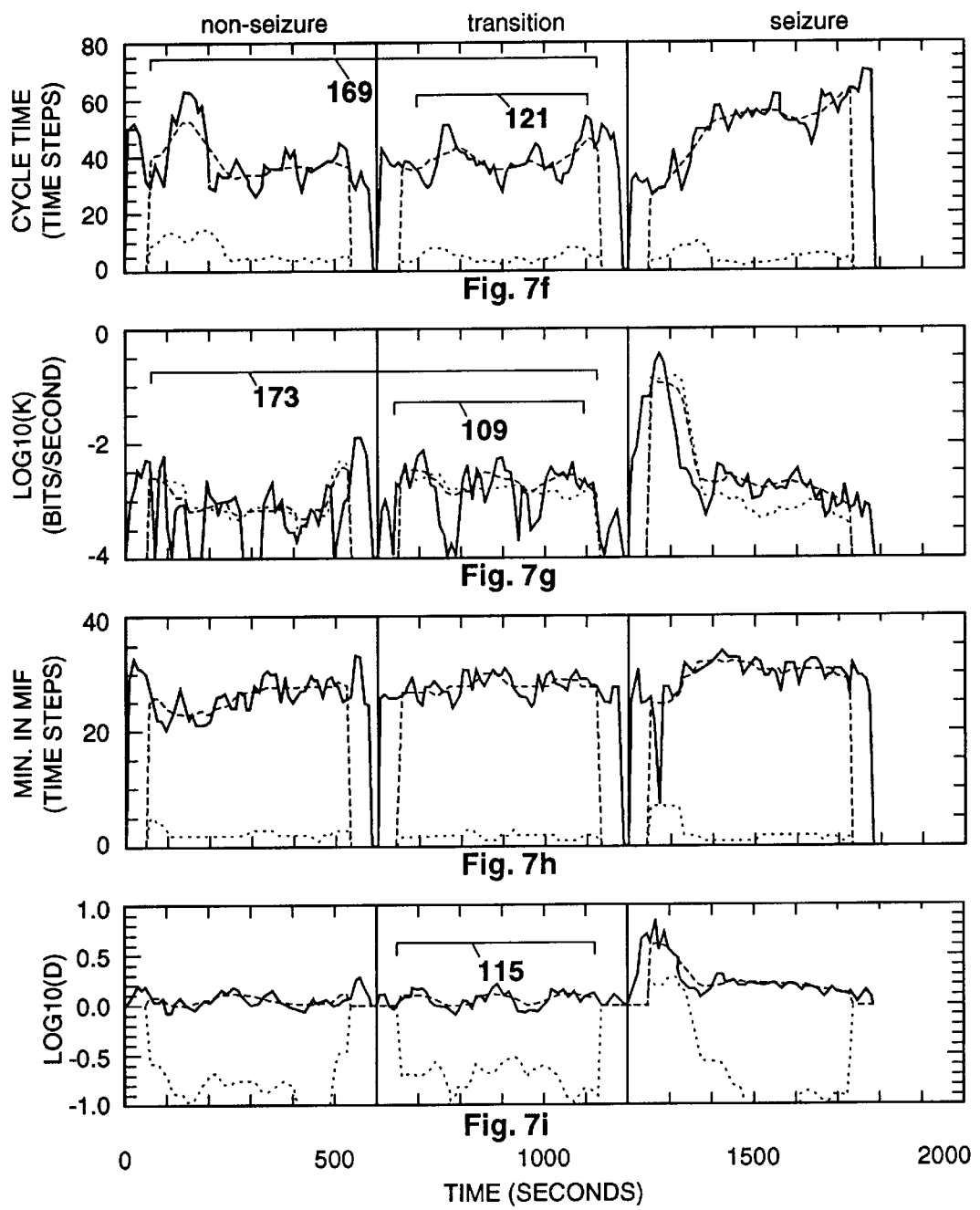

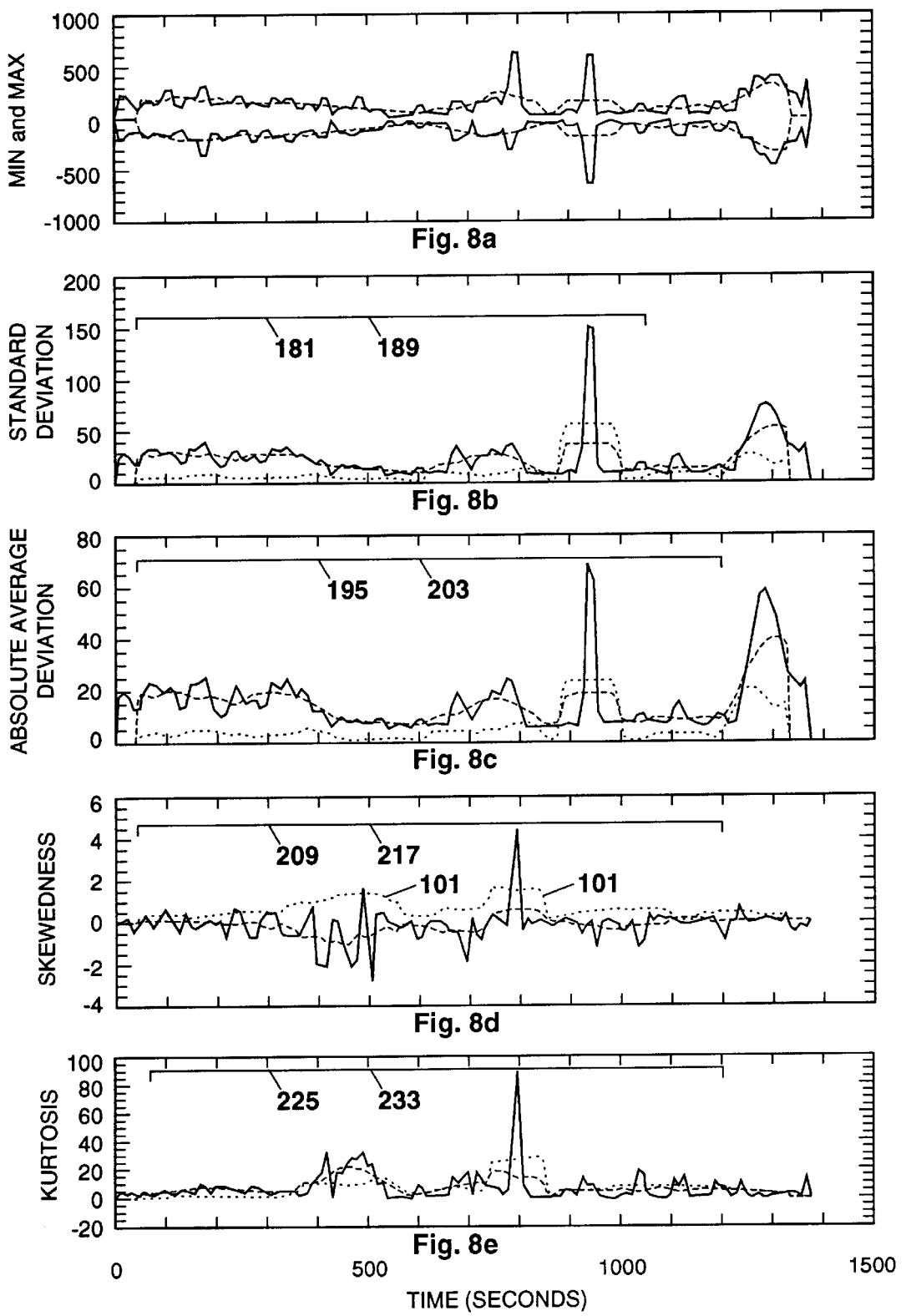

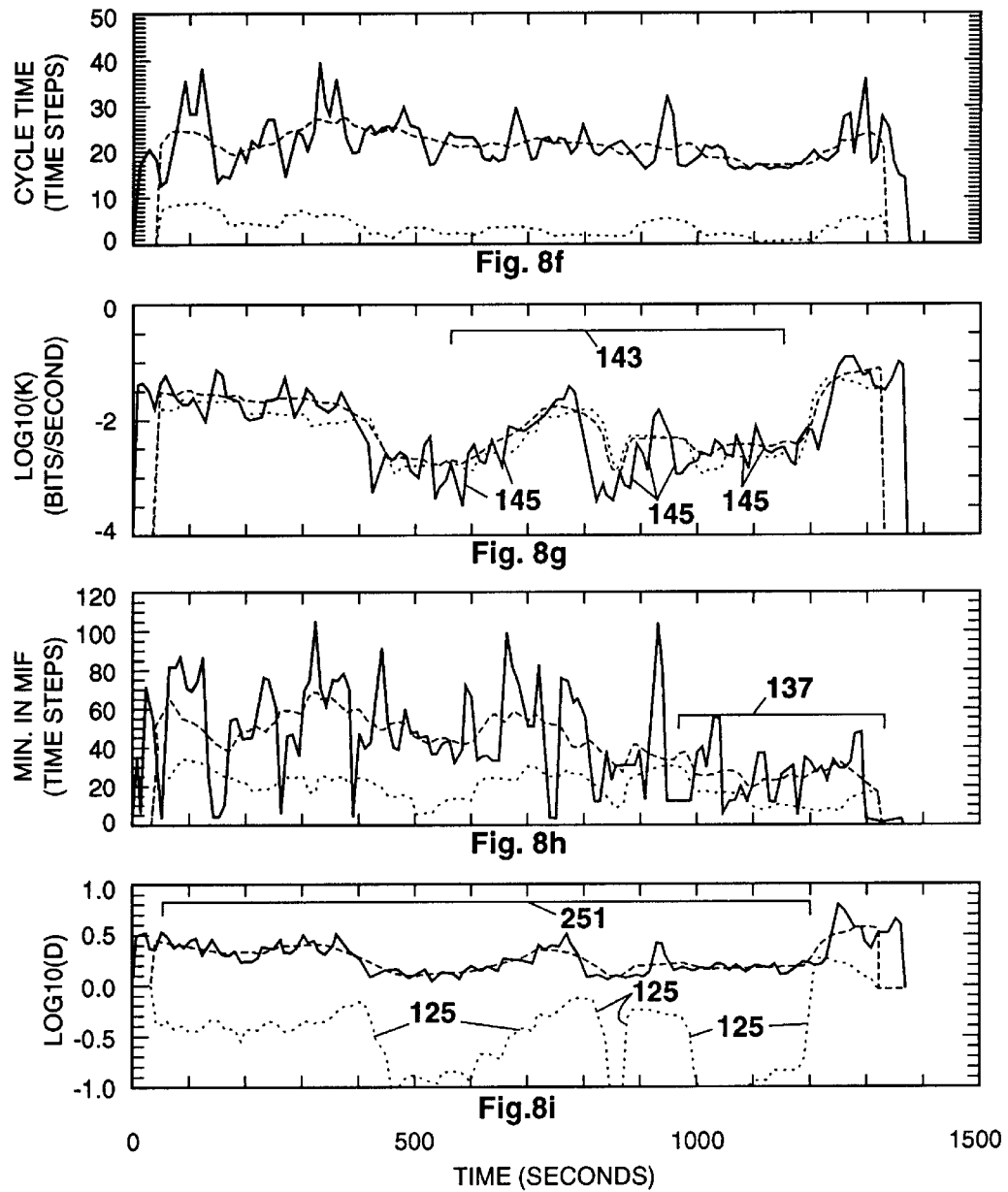

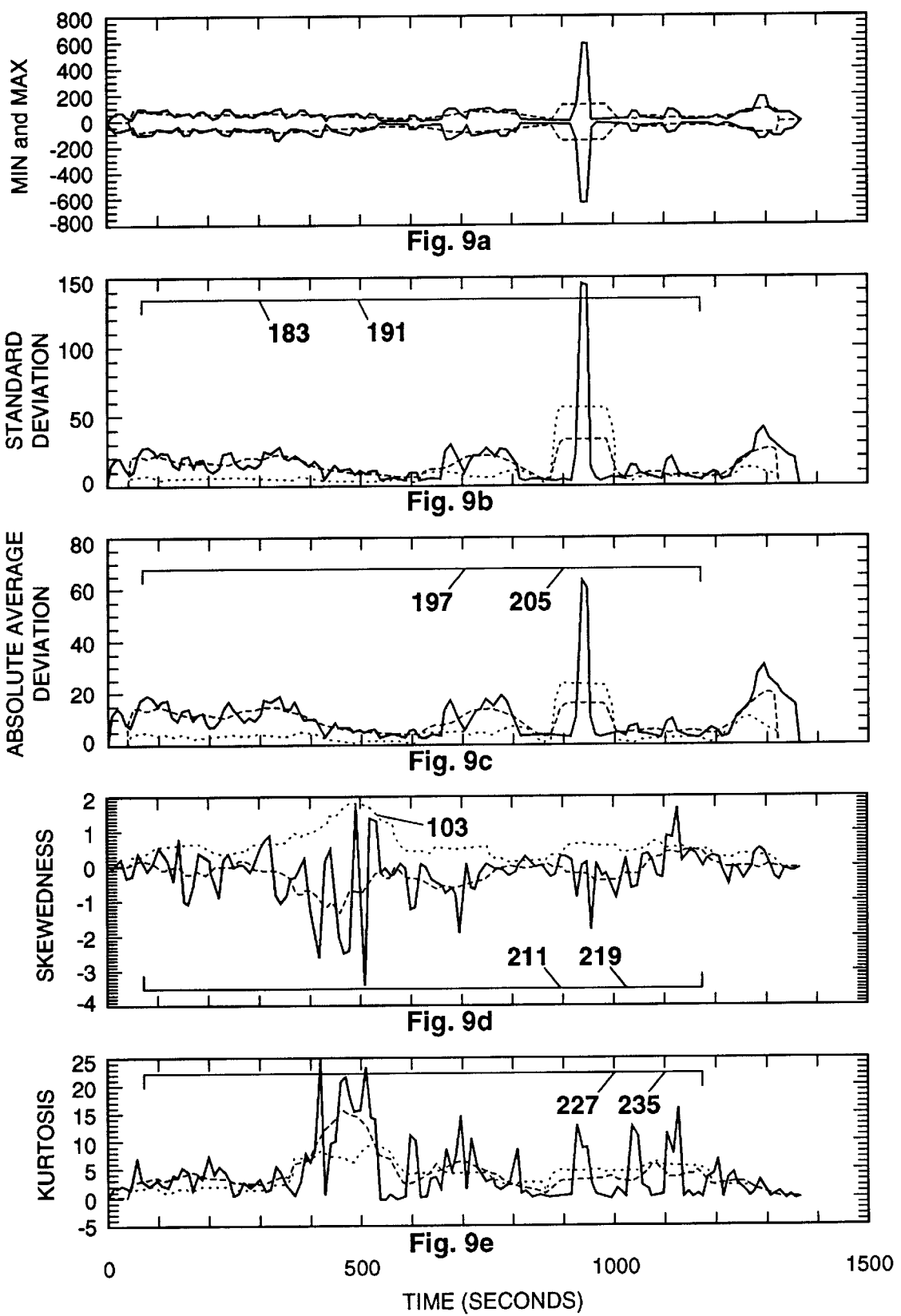

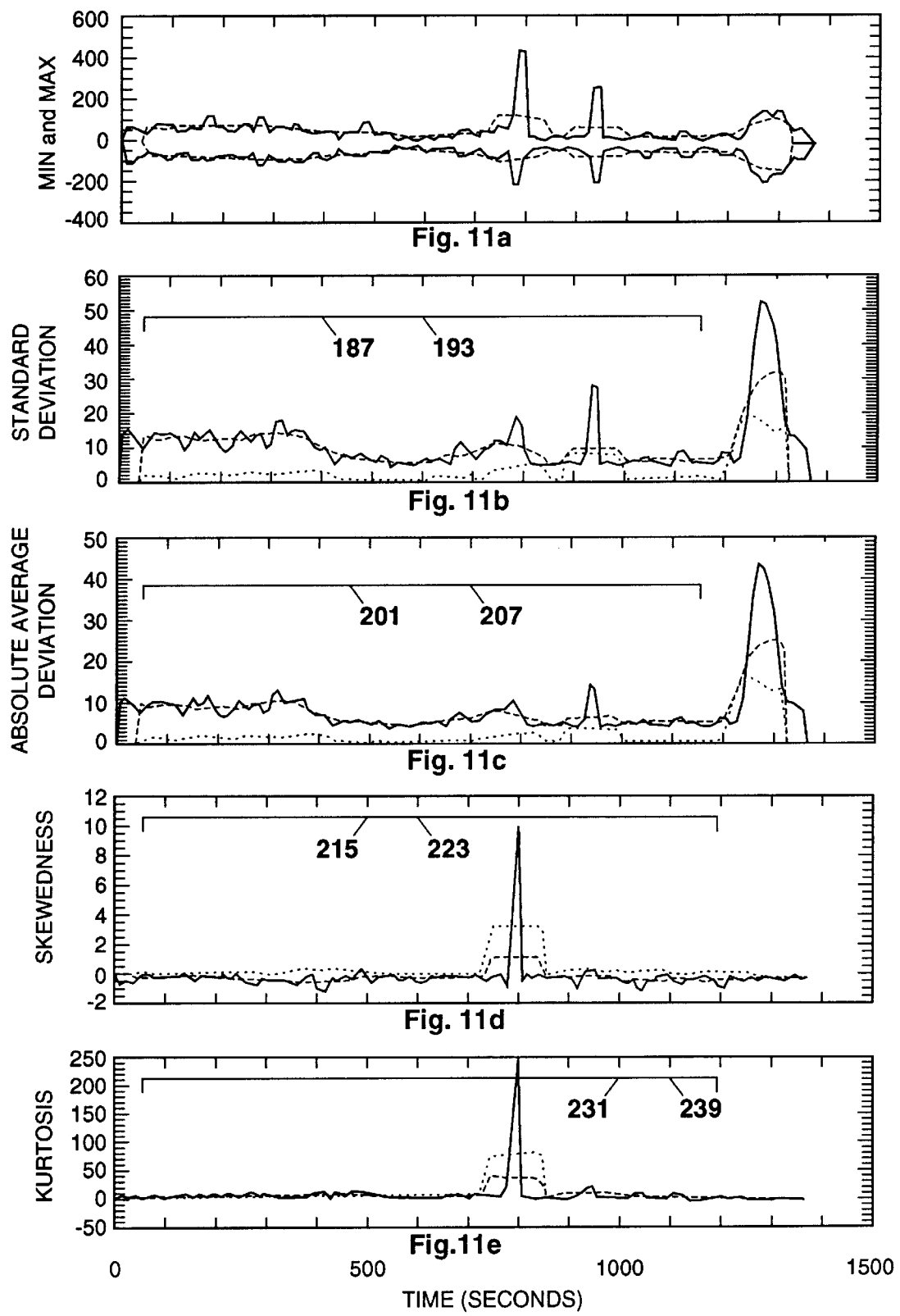

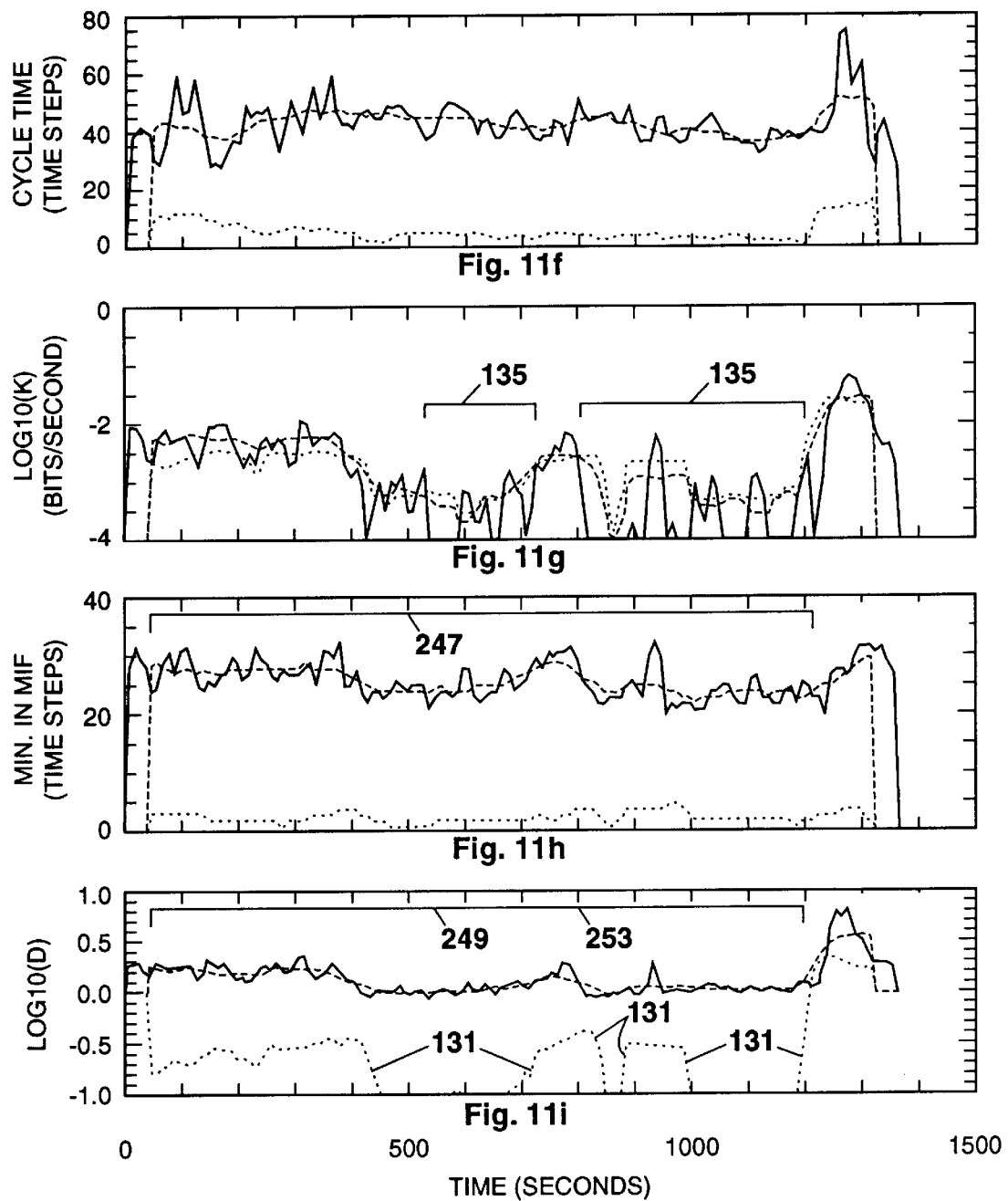

EPILEPTIC SEIZURE PREDICTION BY NON-LINEAR METHODS

The United States Government has rights in this invention pursuant to contract no. DE-AC 05-84OR21400 between the United States Department of Energy and Lockheed Martin Energy Systems, Inc.

FIELD OF THE INVENTION

The present invention relates to the application of chaotic time series analysis (CTSA) to electroencephalogram (EEG) data and magnetoencephalogram (MEG) data, and more particularly to the analysis of the data to predict epileptic seizures.

CROSS-REFERENCE TO RELATED APPLICATIONS

This invention is related to U.S. patent application Ser. No. 08/619,024 Apparatus and Method for Epileptic Seizure Detection Using Non-Linear Methods by Lee M. Hively, Ned E. Clapp, C. Stuart Daw, and William F. Lawkins and to U.S. Pat. No. 5,626,145 Method and Apparatus for Extraction of Low-Frequency Artifacts from Brain Waves for Alertness Detection by Ned E. Clapp and Lee M. Hively, both of which are filed on even date herewith, and both of which are assigned to the same entity.

BACKGROUND OF THE INVENTION

The theory of nonlinear dynamics provides a basis for understanding and potentially controlling many complex physical and engineering systems. An extensive literature exists for nonlinear dynamics in the brain and related work (18). It is well known that brain waves exhibit seemingly random, unpredictable behavior, that is characteristic of deterministic chaos (1, 20). Moreover, chaotic behavior is "normal," while nonchaotic or periodic behavior is indicative of pathophysiology in experimental epilepsy (20). Schiff et al. (11) showed that chemically-induced seizures in rat-brain can be electrically controlled, leading to speculation (4) that human epilepsy may be controlled without drug or surgical intervention. However, effective use of chaos control for epilepsy requires definitive seizure prediction. Thus, this invention diagnoses brain wave data via chaotic time series analysis (CTSA) methods to predict an epileptic seizure.

Nonlinear analysis of neurological diseases via EEG data is extensive. For example, see the 1994 review by Elbert et al. (18). Epilepsy can be recognized only with clear EEG manifestations, but even these seizures are not easy to detect because there is no stereotyped pattern characteristic of all seizures (5). Work by Olsen and colleagues (7) used various linear measures with autoregressive modeling, discriminant analysis, clustering, and artificial neural networks. Valuable nonlinear tools for studying EEG data include correlation dimension, mutual information function, Kolmogorov entropy, phase-space attractors, and largest Lyapunov exponent. No publications or patents apply one or more CTSA measures to EEG data for systematic characterization of non-seizure, seizure, and transition-to-seizure, for prediction of an epileptic seizure.

Very recent analysis by Theiler (16) studied correlation dimension and Lyapunov exponent, using a form of surrogate analysis on a single EEG time series during an epileptic seizure. The surrogate analysis involved a random shuffling of blocks of time serial data, each block containing one quasi-periodic spike-wave complex. The auto-correlation function for the original data is nearly indistinguishable from the surrogate data. The correlation dimension for the original data is significantly different from the surrogate data only at large scale sizes and large embedding dimensions. The maximum Lyapunov exponent ($\lambda$) was negative for both the original and surrogate data and not substantially different, contrary to previous work which found positive $\lambda$ values. Theiler concluded that his analysis suggests a non-linear oscillator with noise on the time scale of the spike-wave complex, but cannot indicate whether chaos exits on a shorter time scale.

DOCUMENT LIST

1. A. Babloyantz and A. Destexhe, "Low-Dimensional Chaos in an Instance of Epilepsy," *Proc. Natl. Acad. Sci. USA* 83, 3513–3517 (1986).
2. D. F. Elliott and K. R. Rao, *Fast Transforms, Analyses, Applications*, Academic Press, 1982.
3. A. M. Fraser and H. L. Swinney, "Independent Coordinates for Strange Attractors from Mutual Information," *Phys. Rev A* 33, 1134–1140 (1986).
4. J. Glanz, "Do Chaos-Control Techniques Offer Hope for Epilepsy?" *Science* 265, 1174 (1994).
5. J. Gotman, "Seizure Recognition and Analysis," *Long-term Monitoring in Epilepsy (EEG Suppl.* No. 37), pgs. 133–145 (1985).
6. G. A. Korn and T. M. Korn, *Mathematical Handbook for Scientists and Engineers*, McGraw-Hill Book Company, New York, 1968.
7. D. E. Olsen, J. A. Cristion, and C. W. Spaur, "Automatic Detection of Epileptic Seizures Using Electroencephalographic Signals," *Johns Hopkins APL Techn. Digest* 12, 182–191 (1991).
8. J. P. M. Pijn, "Quantitative Evaluation of EEG Signals in Epilepsy—Nonlinear Associations, Time Delays, and Nonlinear Dynamics," Ph. D. Thesis, University of Amsterdam, 1990.
9. L. R Rabiner and B. Gold, *Theory and Application of Digital Signal Processing*, Prentice Hall Inc., 1975.
10. S. M. Selby and B. Girling, *Standard Mathematical Tables*, page 390, The Chemical Rubber Co. (14th edition, 1965).
11. S. J. Schiff, K. Jerger, D. H. Duong, T. Chang, M. L. Spano, and W. L. Ditto, "Controlling Chaos in the Brain," *Nature* 370, 615–620 (1994).
12. J. C. Schouten, F. Takens, and C. M. van den Bleek, "Maximum-Likelihood Estimation of the Entropy of an Attractor," *Phys. Rev. E* 49, 126–129 (1994).
13. J. C. Schouten, F. Takens, and C. M. van den Bleek, "Estimation of the Dimension of a Noisy Attractor," *Phys. Rev. E* 50, 1851–1861 (1994).
14. F. Takens, "On the Numerical Determination of the Dimension of an Attractor," in *Dynamical Systems and Bifurcations*, ed. B. L. J. Braaksma, H. W. Broer, and F. Takens, *Lecture Notes in Mathematics* 1125, 99–106 (1984) Springer-Verlag, Berlin.
15. F. J. Taylor, *Digital Filter Design Handbook*, Marcel Dekker, Inc., Publ., New York and Basel, 1983
16. J. Theiler, "On the Evidence for Low-Dimensional Chaos in an Epileptic Electroencephalogram," *Phys. Lett. A* 196, 335–341 (1995).
17. R. C. Watt and S. W Hameroff, "Phase Space Analysis of Human EEG during General Anesthesia," *Ann. N. Y. Acad. Sci.* 504, 286–288 (1987).
18. T. Elbert, W. J. Ray, Z. J. Kowalik, J. E. Skinner, K. E. Graf, N. Birbaumer, "Chaos and Physiology: Deterministic Chaos in Excitable Cell Assemblies," Physiological Reviews 74 (1994)1–47.
19. S. Blanco, R., Quian Ouiroga, O. A. Rosso, and S. Kochen, "Time-frequency analysis of electroencephalogram series," *Physical Review E*, The American Physical Society, Volume 51, Number 3, March 1995
20. S. J. Schiff, K. Jerger, D. H. Duong, T. Chang, M. L. Spano, and W. L. Ditto, "Controlling Chaos in the Brain," *Nature* 370, 615–620 (1994)

OBJECTS OF THE INVENTION

Accordingly, it is an object of the present invention to provide methods and apparatus for predicting epileptic seizures in a patient and providing notification to the patient or to persons who can assist the patient, or to a data collection or transmission means.

Further and other objects of the present invention will become apparent from the description contained herein.

SUMMARY OF THE INVENTION

In accordance with one aspect of the present invention, the foregoing and other objects are achieved by a method for automatically predicting an epileptic seizure in a patient which comprises the steps of: providing at least one channel of a patient's raw brain wave data, called e-data, selected from the group consisting of electroencephalogram data and magnetoencephalogram data; separating the e-data into artifact data, called f-data, and artifact-free data, called g-data, while preventing phase distortions in the data; processing g-data through a low-pass filter to produce a low-pass-filtered version of g-data, called h-data; applying at least one measure selected from the group of consisting of the linear statistical measures minimum and maximum, standard deviation, absolute minimum deviation, skewedness, and kurtosis, and the nonlinear measures time steps per cycle, Kolmogorov entropy, first minimum in the mutual information function, and correlation dimension to at least one type of data selected from the group consisting of e-data, f-data, g-data, and h-data to provide at least one time serial sequence of nonlinear measures, from which at least one indicative trend selected from the group consisting of abrupt increases, abrupt decreases, peaks, valleys, and combinations thereof is determined; comparing at least one indicative trend with at least one known seizure predictor; and determining from said comparison whether an epileptic seizure is oncoming in the patient.

In accordance with a second aspect of the present invention, the foregoing and other objects are achieved by apparatus for automatically predicting an epileptic seizure in a patient which comprises: data provision means for providing at least one channel of raw brain wave data, called e-data, selected from the group consisting of electroencephalogram data and magnetoencephalogram data; separation means for separating e-data into artifact data, called f-data, and artifact-free data, called g-data, while preventing phase distortions in the data, communicably connected to said data provision means; low-pass filter means for filtering g-data to produce a low-pass filtered version of g-data, called h-data, communicably connected to said separation means; application means for applying at least one measure selected from the group consisting of the linear statistical measures minimum and maximum, standard deviation, absolute minimum deviation, skewedness, and kurtosis, and the nonlinear measures time steps per cycle, Komogorov entropy, first minimum in the mutual information function, and correlation dimension to at least one type of data selected from the group consisting of e-data, f-data, g-data, and h-data to provide at least one time serial sequence of nonlinear measures, from which at least one indicative trend selected from the group consisting of abrupt increases, abrupt decreases, peaks, valleys, and combinations thereof is determined, communicably connected to said low-pass filter means; comparison means for comparing at least one indicative trend with known seizure indicators, connected to said application means; and, determination means for determining from the comparison whether an epileptic seizure is oncoming in the patient, communicably connected to said comparison means.

BRIEF DESCRIPTION OF THE DRAWINGS

In the drawings:

FIGS. 4, 5, 6, and 7 show linear and nonlinear measures of time serial data for Example I. FIG. 4 shows linear and nonlinear measures of raw (e-data); FIG. 5 shows linear and nonlinear measures of artifact (f-data); FIG. 6 shows linear and nonlinear measures of artifact-filtered (g-data); and FIG. 7 shows linear and nonlinear measures of artifact- and low-pass-filtered (h-data). Various mathematical properties and characteristics are shown for each data type, and are further shown in parts (a), (b), (c), (d), (e), (f), (g), (h), and (i) for each data type. These measures are shown as curves, each curve representing a time serial sequence of linear or nonlinear measures. Within each curve, significant features such as abrupt increases, abrupt decreases, peaks, and valleys may be viewed as indicative trends which are then compared to trends which have been shown to be siezure predictors. Thus from the comparison it can be determined whether a siezure is oncoming in the patient. In parts (a), (b), (c), (d), and (e) for each data type, the solid line is the specific measure, the dashed line is the 11-point average, and the dotted line is the standard deviation for the measure.

FIGS. 8, 9, 10, and 11 show linear and nonlinear measures of time serial data for Example II. FIG. 8 shows linear and nonlinear measures of raw (e-data); FIG. 9 shows linear and nonlinear measures of artifact (f-data); FIG. 10 shows linear and nonlinear measures of artifact-filtered (g-data); and FIG. 11 shows linear and nonlinear measures of artifact- and low-pass filtered (h-data). Various mathematical properties and characteristics as computed for each data type are further shown in parts (a), (b), (c), (d), (e), (f), (g), (h), and (i) for each data type. These measures are shown as curves, each curve representing a time serial sequence of linear or nonlinear measures. Within each curve, significant features such as abrupt increases, abrupt decreases, peaks, and valleys may be viewed as indicative trends which are then compared to trends which have been shown to be siezure predictors. Thus from the comparison it can be determined whether a siezure is oncoming in the patient. In parts (a), (b), (c), (d), and (e) for each data type, the solid line is the specific measure, the dashed line is the 11-point average, and the dotted line is the standard deviation for the measure.

Figure 1:
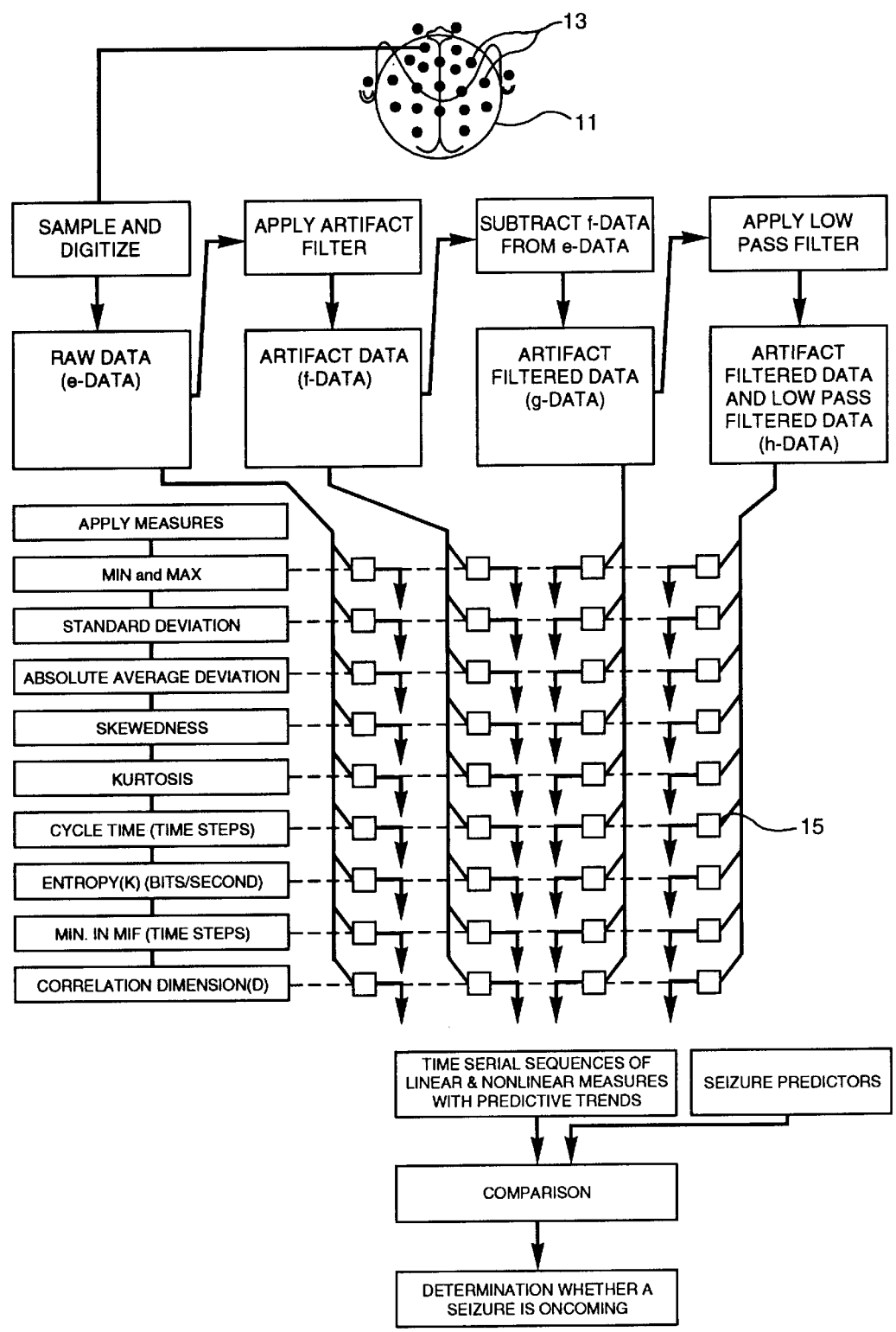
FIG. 1 is a block diagram showing how, in accordance with the present invention, brain wave data is obtained from the patient, digitized, processed, and analyzed by nonlinear methods to predict epileptic seizures.

For a better understanding of the present invention, together with other and further objects, advantages and capabilities thereof, reference is made to the following disclosure and appended claims in connection with the above-described drawings.

DETAILED DESCRIPTION OF THE INVENTION

Chaotic time series analysis (CTSA) is applied to human electroencephalogram (EEG) and magnetoencephalogram (MEG) data. For reference, equation numbers are shown at the right of each equation.

In Examples I and II, EEG data from three epochs were examined: epileptic seizure, non-seizure, and transition from non-seizure to seizure. The CTSA tools were applied to four forms of these data: raw EEG data (e-data), artifact data (f-data) via application of a quadratic zero-phase filter of the raw data, artifact-filtered data (g-data) that was the residual after subtracting f-data from e-data, and a low-pass-filtered version of g-data (h-data). The transition from normal to seizure state also is characterized by distinctly different trends in the nonlinear and linear measures, as seizure predictors. Several linear and nonlinear measures distinctly predict an epileptic seizure, including sample standard deviation of the correlation dimension for e-data having small variation during non-seizure but undergoing large rises and falls during transition from non-seizure to seizure; sample standard deviation for the correlation dimension of f-data having small variation during non-seizure but undergoing large rises and falls during transition from non-seizure to seizure; sample standard deviation for the correlation dimension of g-data having small variation during non-seizure but undergoing large rises and falls during transition from non-seizure to seizure; sample standard deviation of the correlation dimension for h-data having small variation during non-seizure but undergoing large rises and falls during transition from non-seizure to seizure; the Kolmogorov entropy for f-data having large, aperiodic variations during transition from non-seizure to seizure and less variation during non-seizure; the Kolmogorov entropy for h-data having large, aperiodic variations during transition from non-seizure to seizure and less variation during non-seizure; a gradual decrease in the first minimum for the Mutual Information Function for the e-data; a gradual decrease in the first minimum for the Mutual Information Function in the g-data; the average Kolmogorov entropy for e-data rising monotonically while the Kolmogorov entropy undergoes oscillations of increasing amplitude about the average Kolmogorov entropy, then decreasing abruptly and repeating cyclically; and the variability in skewedness and kurtosis for f-data being moderate with small sample standard deviations then increasing markedly with large sample standard deviations subsequently with the skewedness returning to moderate values while the sample standard deviation of the kurtosis remaining at 2 to 3 times the non-seizure value. Analysis of e-data shows that statistically significant nonlinear structure is present during the non-seizure, transition, and seizure epochs.

Figure 2:
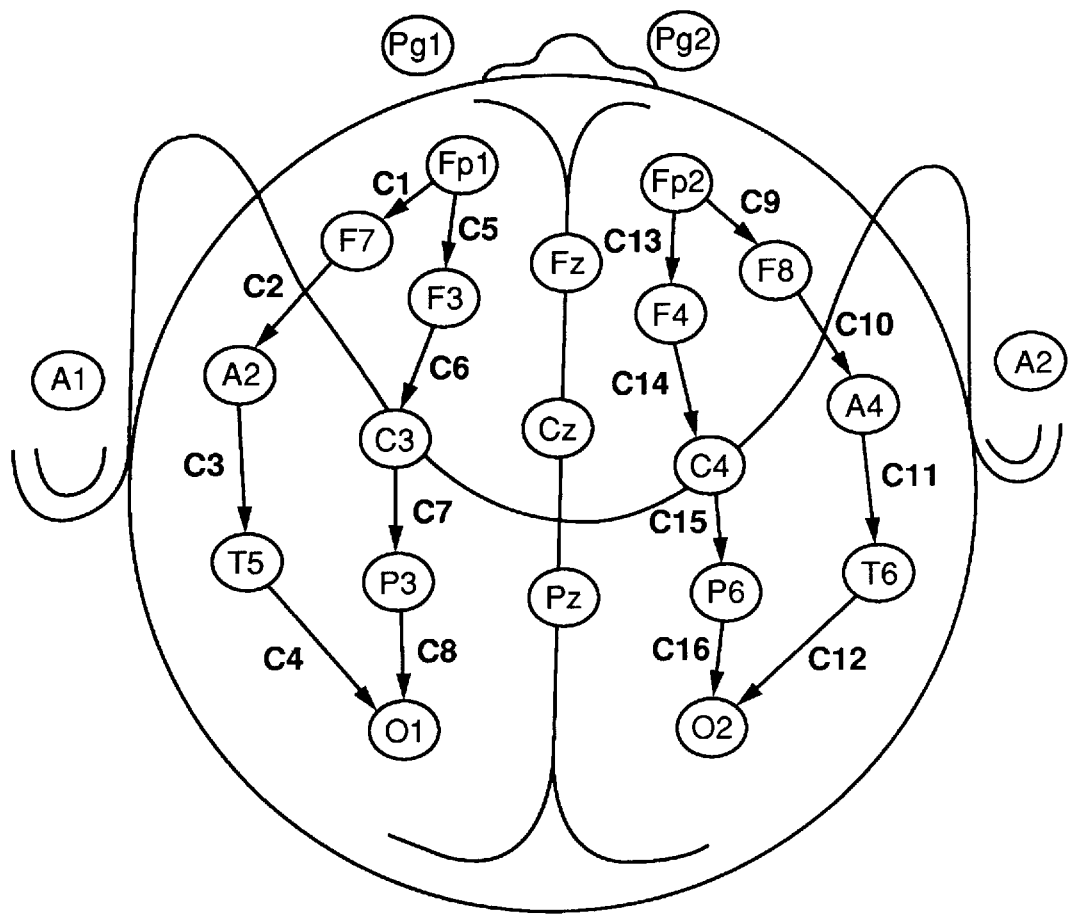
FIG. 2 shows standard EEG electrode positions on a patient's scalp for the bipolar montage, looking from above, as utilized in Examples I and II.

Two sets of channel-13 EEG data from one patient are provided as examples. In FIG. 1 of the drawings, 11 shows the patient's head, looking from above. 13 shows EEG electrode positions on the patient's scalp. 15 shows a nonlinear measure of EEG data. In FIG. 2 of the drawings, C13 labels the position where the channel 13 data, which is used in this work, originates. Analysis of C13 data was chosen for these examples to demonstrate the robust removal of eye-blink artifact, which otherwise dominates channel 13 because of its proximity to the eye. This method and apparatus can be applied to data from other EEG channels, as well as to MEG data, as is apparent to those skilled in the art. Both sets of data included non-seizure, transition-to-seizure, and epileptic seizure data. The analysis included various linear measures (standard deviation, absolute average deviation, skewedness, kurtosis), plus nonlinear measures (time steps per cycle, Kolmogorov entropy, first minimum in the mutual information function, and correlation dimension). Four forms of the data were analyzed: raw EEG (e data), artifact (f data) via application of a zero-phase quadratic filter, artifact-filtered (g data) that was the residual after subtracting f-data from g-data, and a low-pass-filtered version of the g-data (h data). Both linear and nonlinear measures provide trends to predict seizure onset. Nonlinear tools identified predictive trends with and without artifact removal, with and without low-pass filtering, demonstrating the robustness of these methods to noise and artifacts. Surrogate analysis of e-data showed that this data has significant nonlinear structure.

Analysis in accordance with the present invention reveals trends in linear and nonlinear measures that precede the seizure by 500–800 seconds, as shown in FIGS. 4–11 and as described further herein. These trends are easily computable and permit seizure prediction. Transition indicators are somewhat different for the two seizure examples. This indicates that siezure indicators that are chosen for comparison with indicative trends for siezure prediction in a patient must be chosen carefully.

In the examples described herein, sixteen channels of EEG data were analyzed in the bipolar montage, as illustrated in FIG. 2. The data were retrieved in analog form from VHS tapes and converted to digital form with 12-bit precision, giving an integer between −2048 and +2047. The digital sampling rate ($f_s$) was 512 Hz over a total sample time of 10–23 minutes, corresponding to a total dataset size of 9.8–22.5 megabytes in binary form. Three epochs of data were examined: epileptic seizure and post-seizure, non-seizure, and transition from non-seizure state to seizure (transition).

It is acknowledged that to predict an epileptic seizure prior to its occurrence, the brain wave data used would not be recorded data, but would be currently-occurring data. This data would be taken from the patient to the apparatus directly using standard EEG or MEG methods, or indirectly by transmitting the data to an apparatus remote from the patient by means such as telephone, radio, or other communications means well known to the skilled artisan.

Raw brain wave data contains not only signals associated with brain activity, but also has artifacts (e.g., eye blinks, muscle twitches, chewing, etc.) that obscure the brain-wave data signal. In order to observe artifact-free data and artifact data independently, the raw data must be separated into artifact data and artifact-free data. A zero-phase filter was developed and used to remove low-frequency artifacts, based on the following criterion. A zero-phase-shift filter was needed to prevent phase distortions when subtracting the filter output (the "artifact" data signal) from the raw data signal to yield an undistorted artifact-filtered or artifact-free signal, because phase relationships are most important in the subsequent nonlinear analysis. Standard high-pass filter techniques do not meet this criterion. A computationally fast, simple, low-frequency signal follower was necessary to eventually apply the filter in real- or near-real time. Consequently, quadratic regression analysis was used, with the same number of data samples on either side of a central point. Other standard digital filtering methods (15) could not meet this requirement.

The zero-phase filter method and apparatus, which may be embodied in various ways well known to one skilled in the art, such as a specially-programmed computer or a programmed integrated circuit, semi-conductor chip, or micro-processor, is as follows. For a specific channel, the brain-wave signal (e) at time (t) is sampled at regular intervals ($t_i=i\Delta t$) to yield a set of time serial data $e_i=e(t_i)$. A filter-window length was chosen of $2n+1$ points from the time series, where n is the number of points on either side of the central point ($e_c$) as indicated in the sequence below.

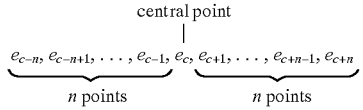

The data was fitted to a quadratic equation that takes the form: $F_i=F(t_i)=a_1(t_i-t_c)^2+a_2(t_i-t_c)+a_3=a_1T_i^2+a_2T_i+a_3$. Here, $t_c=c\Delta t$ is the time at the central point, and $T_i=t_i-t_c$. This approximation is fitted to the data, by minimizing the sum of squares of the differences between the quadratic equation, $F(t)$, and the raw EEG data, $e(t)$, corresponding to the minimum in the following function:

$$L = \sum_{i=c-n}^{c+n} [F(t_i) - e(t_i)]^2 = \sum_{i=-n}^{n} [(a_1T_i^2 + a_2T_i + a_3) - e_{i+c}]^2 \quad \text{Eq. 1}$$

The minimum in L is found from the condition $\partial L/\partial a_k=0$, for $k=\{1, 2, 3\}$, forming three simultaneous linear equations in three unknowns. The window-averaged artifact ($F_c$) is given by the fitted value of the central point, $F_c=F(0)=a_3$. Note that the sums over odd powers of $T_i$ are zero and that symmetric sums over even powers of $T_i$ (over i from $-n$ to $+n$) can be converted to sums from 1 to n with $T_i=i\Delta t$, yielding a window-averaged solution for the artifact signal:

$$F_c = \frac{3(3n^2 + 3n - 1)\left(\sum_i e_{i+c}\right) - 15\left(\sum_i i^2 e_{i+c}\right)}{(4n^2 + 4n - 3)(2n + 1)} \quad \text{Eq. 2}$$

Here, $\Sigma_i$ indicates the sum over i from $-n$ to $+n$. Sums over even powers of "i" were explicitly evaluated with standard formulae (10). The effort to evaluate $F_c$ can be reduced substantially by computing the sums initially from Eq.2 (at $c=n+1$), and then using the following recursions thereafter:

$$\sum_{i=-n}^{n} e_{i+c+1} = e_{c+n+1} - e_{c-n} + \sum_{i=-n}^{n} e_{i+c} \quad \text{Eq. 3}$$

$$\sum_{i=-n}^{n} ie_{i+c+1} = ne_{c+n+1} - (n-1)e_{c-n} + \sum_{i=-n}^{n} ie_{i+c} - \sum_{i=-n}^{n} e_{i+c} \quad \text{Eq. 4}$$

$$\sum_{i=-n}^{n} i^2 e_{i+c+1} = \quad \text{Eq. 5}$$

$$n^2 e_{c+n+1} - (n+1)^2 e_{c-n} + \sum_{i=-n}^{n} i^2 e_{i+c} - 2\sum_{i=-n}^{n} ie_{i+c} + \sum_{i=-n}^{n} e_{i+c}$$

The right-hand sides of Eqs. 3–5 only involve the sums previously computed. Application of Eqs. 2–5 to the N-point set of original time serial EEG data ($e_i$, illustrated as the dotted curve in FIG. 3a) yields an artifact dataset ($f_i$ or f-data, illustrated as the solid curve in FIG. 3a) with (N-2n) points that contains the low frequency artifact signal. The residual signal ($g_i$ or g-data, illustrated as the solid curve in FIG. 3b) is the difference, $g_i=e_i-f_i$, and is a signal that is free of low-frequency artifacts. Subsequently, we apply a standard fourth-order low-pass filter at 50 Hz (e.g., see Ref. 9) to the g-data, to yield artifact-filtered, low-pass-filtered data ($h_i$ or h-data) that is free of both low- and high-frequency artifacts. Note that spike-wave phenomena at 100 Hz in h-data are attenuated by 28 db (a factor of 25), while the g-data retain the full spike-wave signals. A standard second-order, third-order, or fourth order filter at frequencies between about 35 Hz and about 60 Hz would also be effective as a low-pass filter.

Figure 3A:
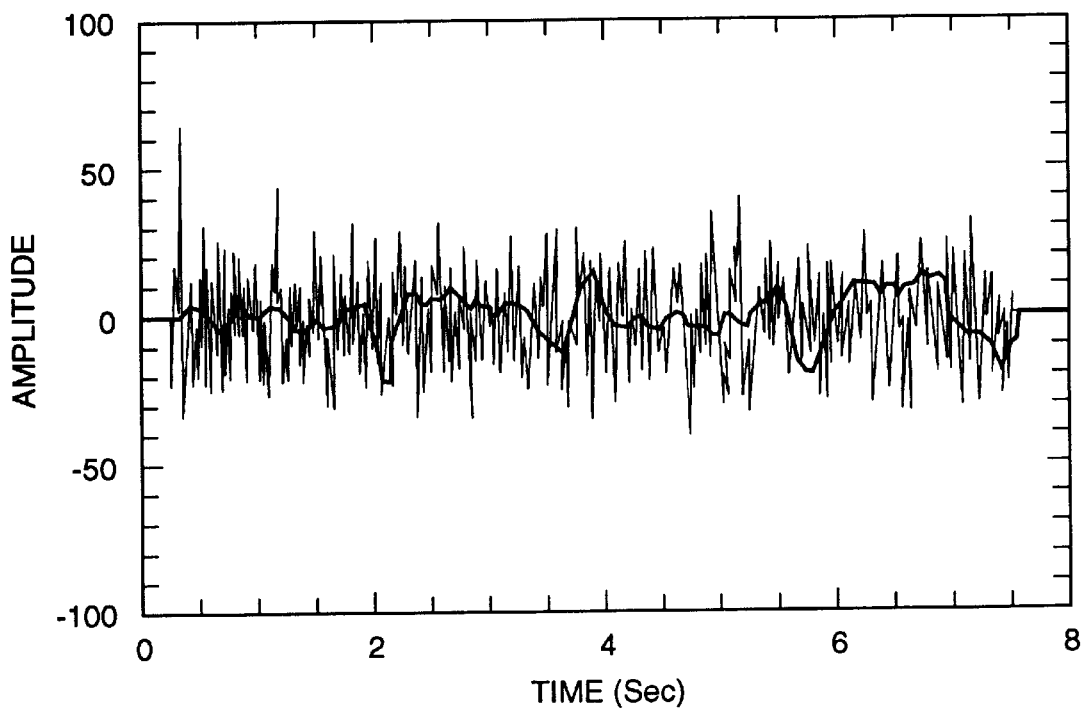
FIG. 3 shows sample plots of EEG data, to illustrate raw data (e-data as the dotted curve in FIG. 3a), and artifact-filtered data (g-data, shown in FIG. 3b), as an example of the method and apparatus of this invention.
Figure 3B:
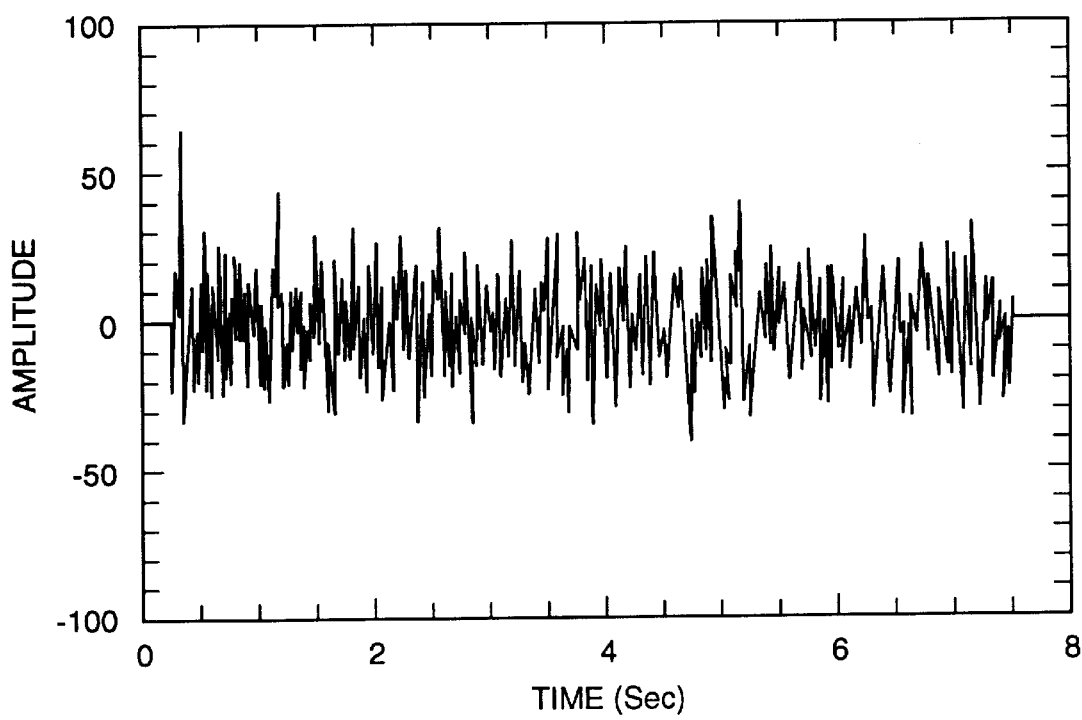
Figure 5F:
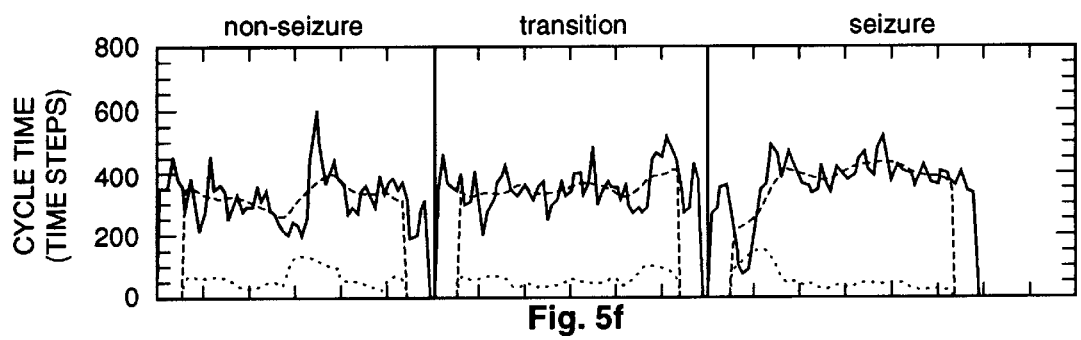
Figure 5G:
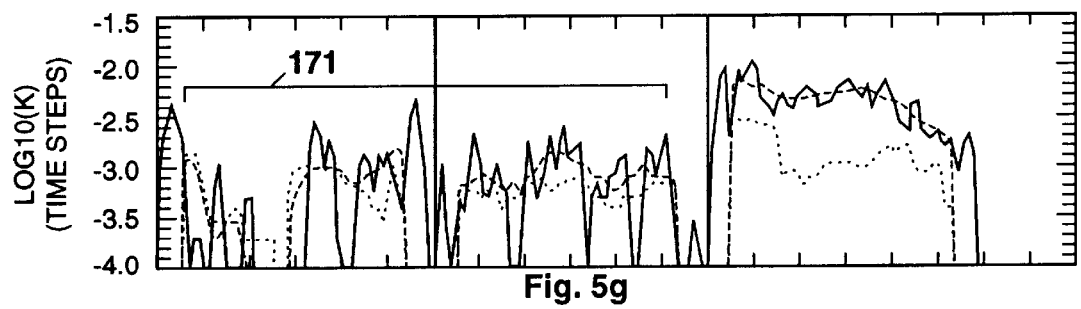
Figure 5H:
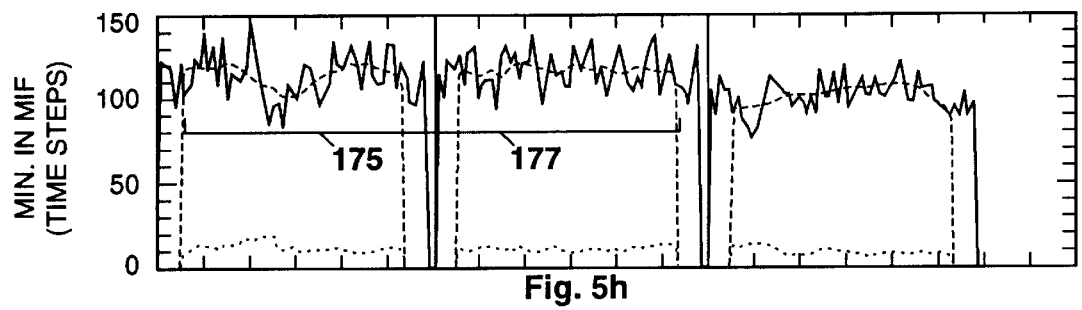
Figure 5I:
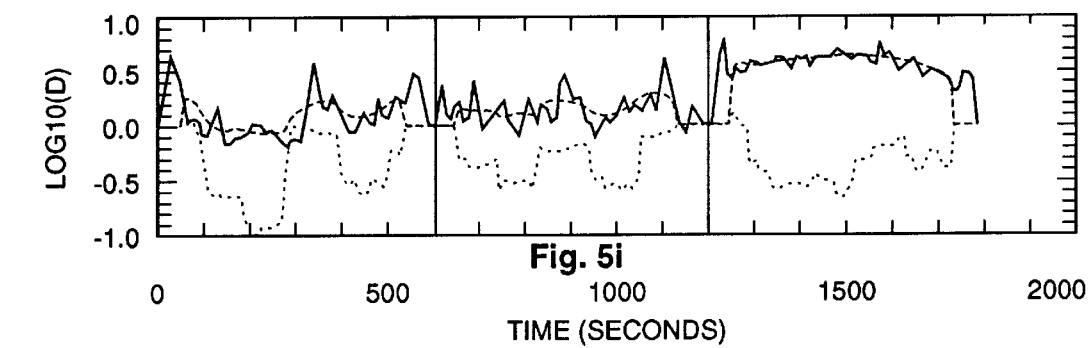
Figure 9F:
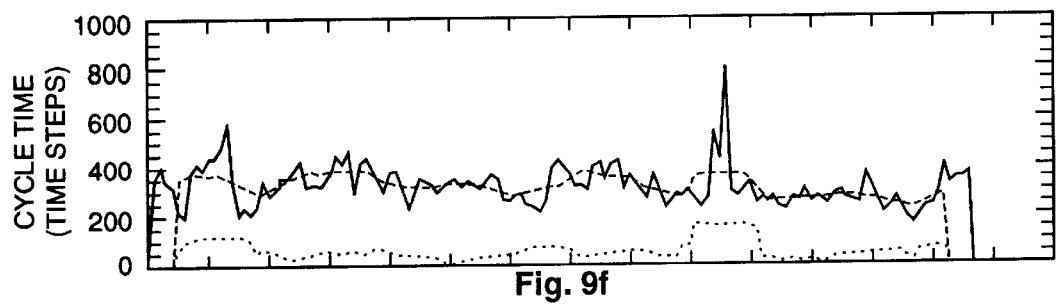
Figure 9G:
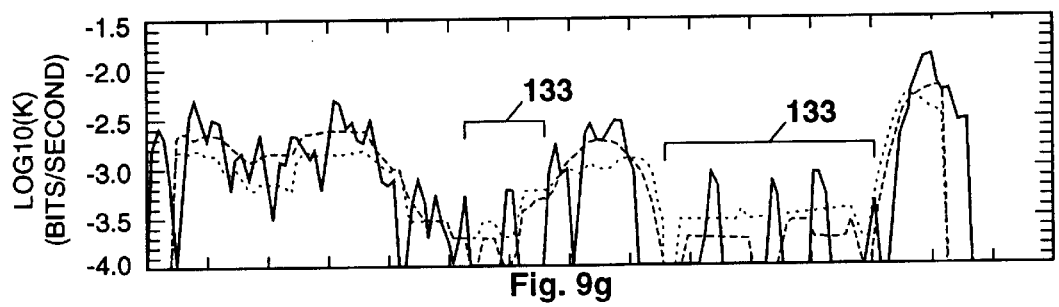
Figure 9H:
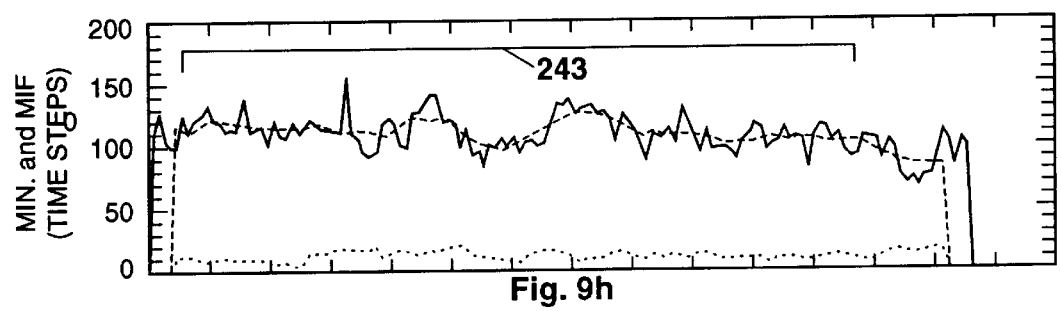
Figure 9I:
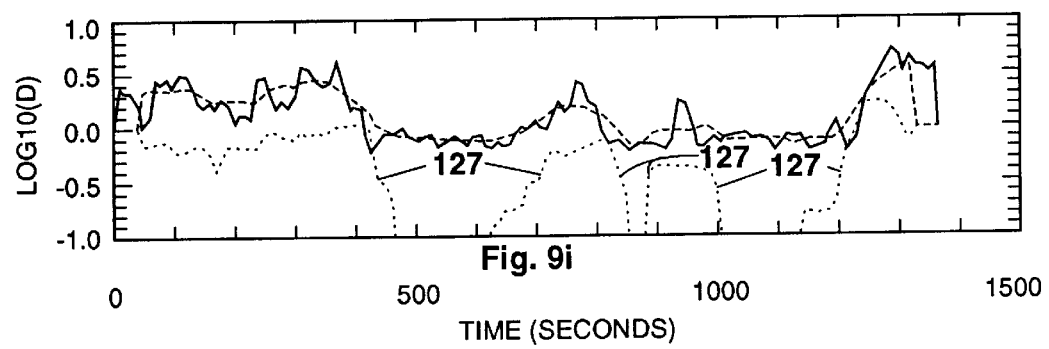
Figure 10A:
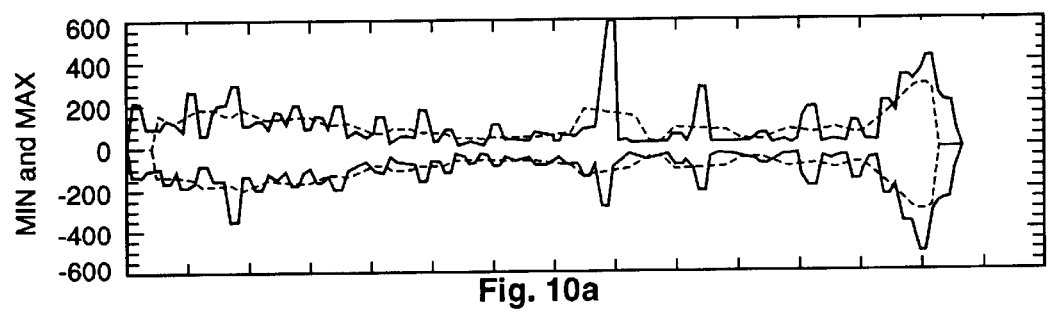
Figure 10B:
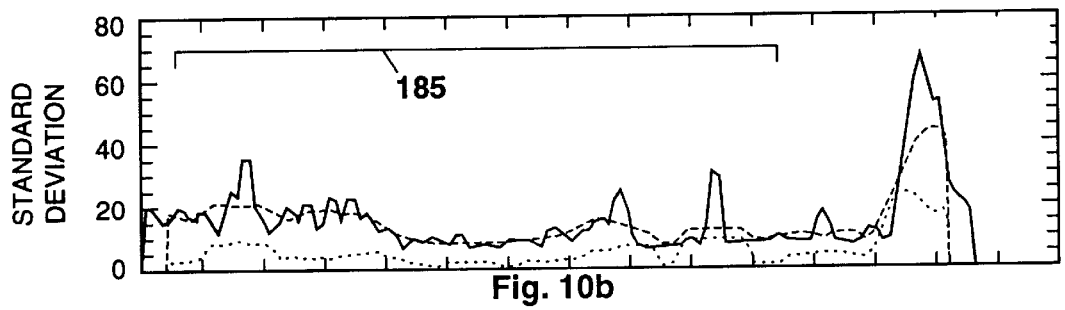
Figure 10C:
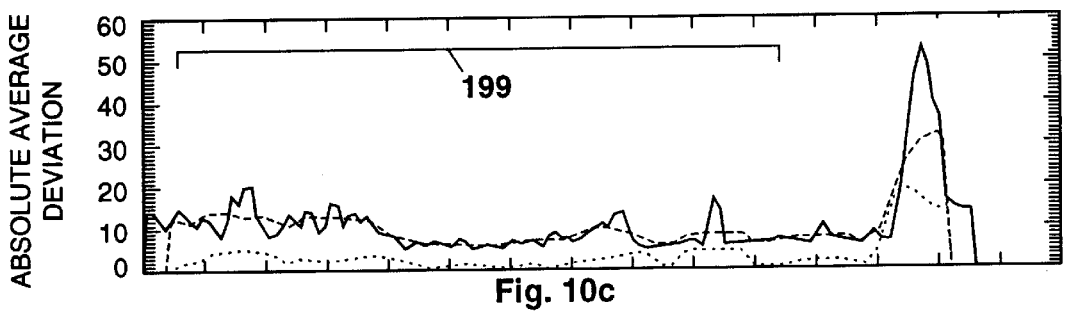
Figure 10D:
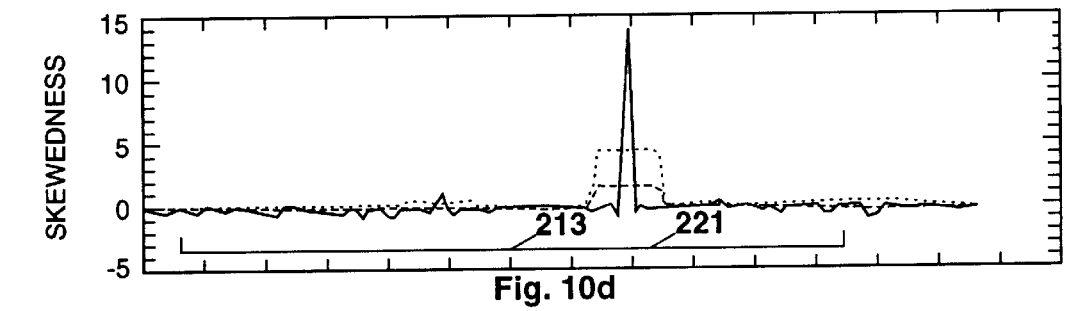
Figure 10E:
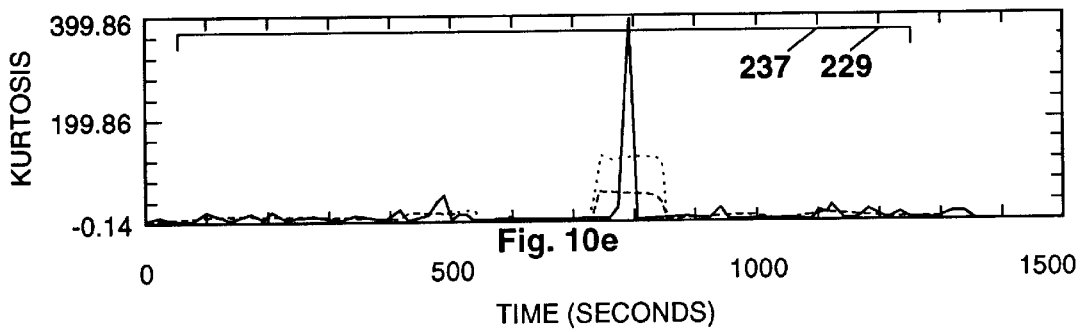
Figure 10F:
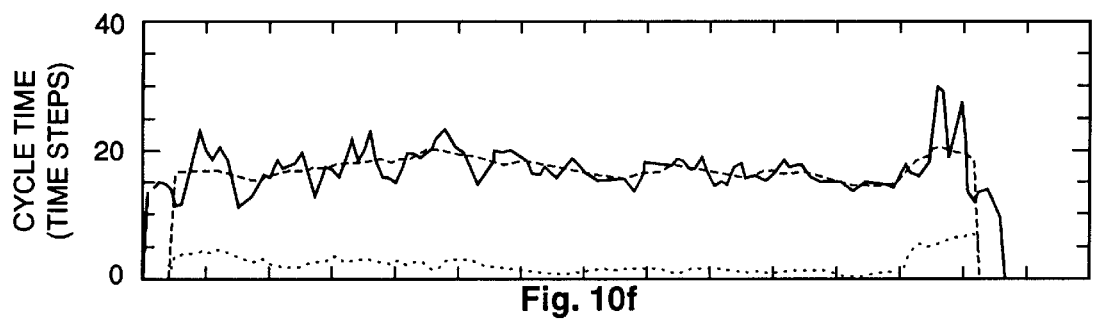
Figure 10G:
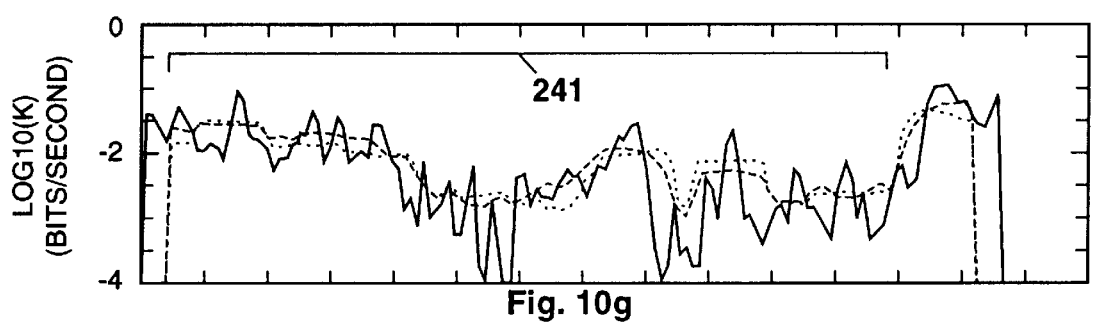
Figure 10H:
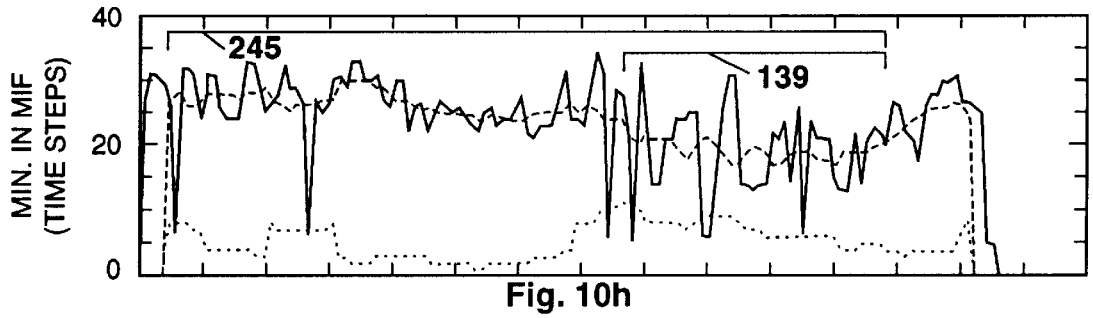
Figure 10I:
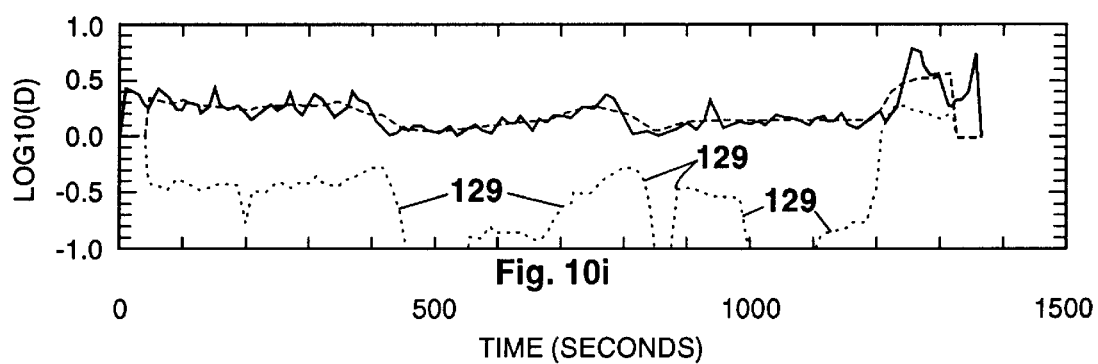

The filter-window length (n=128) corresponds to a frequency of 2.0 Hz [=512 Hz/(2n+1)]. FIG. 3a shows an example of the application of this method, with (raw) e-data in light gray and a superimposed (dark line) artifact signal (f-data), which clearly follows the low-frequency trends. FIG. 3b shows the residual signal (g-data) for this example, as having little low-frequency component while retaining the higher frequency information.

For a specific EEG channel, a time history of the nonlinear measures was obtained by applying the CTSA tools to a series of 20-second analysis-windows of the four data types (e, f, g, h). These data are designated herein as $x_i$. The length of the analysis window (w) was 10,240 points. Each analysis-window had a 5,120-point overlap with the previous (or next) analysis-window of data. This 50% overlap provides an optimal mix of new and old data for smooth time-history trend generation (2), as illustrated below.

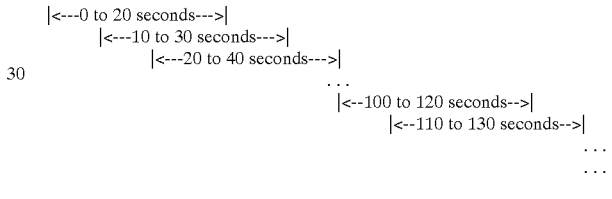

The zero-phase quadratic filter provides artifact-filtered data with frequencies of $\geq 2$ Hz. A heuristic for (linear) Fourier analysis is that $\geq 10$ periods of data are required to faithfully recover cyclic information at a specific frequency. Thus, $\geq 5$ seconds of data are needed to obtain Fourier amplitude and phase information at a signal frequency of 2 Hz. However, this heuristic does not apply to nonlinear analysis. For example, 20 seconds of data are necessary to obtain consistent results for the Kolmogorov entropy. This need for longer dataset lengths (~10,000 points) for consistent nonlinear measures conflicts with the need for shorter dataset lengths ($\geq 5,000$ points) to provide adequate resolution for the time history generation of trends. Consequently, a 20-second analysis window was used, as described above, with a 50% overlap for an effective time history resolution of 10 seconds. The nonlinear measures for each 20-second analysis window were associated with the time at the center of the analysis window, i.e., every ten seconds. The nonlinear measures for each 20-second analysis window were associated with the time at the center of the analysis window, i.e., every ten seconds. Shorter or longer analysis window lengths can be used in proportion to higher or lower data sampling rates, as is obvious to those skilled in the art.

Many characterization tools exist for chaotic data analysis. A subset of the tools that were found in previous work to be good measures for EEG data were used in carrying out the present invention. These tools include the following: standard statistical measures (minimum, maximum; average, absolute average deviation, standard deviation, skewedness, kurtosis, time per cycle); Kolmogorov entropy and entropy spectrum; mutual information function; maximum likelihood correlation dimension and correlation dimension spectrum; surrogate generation and nonlinearity tests; and nonlinear digital filters (as discussed herein).

Entropy, correlation dimension, and mutual information were used in the present invention as nonlinear measures for seizure analysis. The first minimum in the mutual information defines the time scale for generating the return map for EEG dynamics. The return map underlies the correlation dimension (measure of dynamic complexity) and entropy (measure of dynamic predictability). We have applied these same measures successfully in analyzing other systems.

The statistical measures for the present study are obtained by standard methods (6). The maximum and minimum are obtained as maximum and minimum (respectively) over the $x_i$ values in a time-serial window of w points. The average ($\underline{x}$) is given by:

$$\underline{x} = \left(\frac{1}{w}\right) \sum_{i=1}^{w} x_i \qquad \text{Eq. 6}$$

The r-th order moment ($m_r$) of the x-data is:

$$m_r = \left(\frac{1}{w}\right) \sum_{i=1}^{w} (x_i - \underline{x})^r \qquad \text{Eq. 7}$$

The absolute average deviation (a) provides a robust indicator of the $x_i$. variability (13) and is defined as:

$$a = \left(\frac{1}{w}\right) \sum_{i=1}^{w} |x_i - \underline{x}| \qquad \text{Eq. 8}$$

An unbiased estimate of the standard deviation ($\sigma$) is:

$$\sigma = \left[\frac{wm_2}{w-1}\right]^{1/2} \qquad \text{Eq. 9}$$

An estimate for the skewness (s) is:

$$s = \frac{m_3}{m_2^{3/2}} \qquad \text{Eq. 10}$$

An estimate for the kurtosis (k) is:

$$k = \frac{m_4}{m_2^2} - 3 \qquad \text{Eq. 11}$$

The average cycle time ($T_c$) is important as a characteristic time of the nonlinear system:

$$T_c = \frac{\text{window length in timesteps}}{\left(\frac{\text{number of mean crossings}}{2}\right)} \qquad \text{Eq. 12}$$

The mutual information function (MIF) is a nonlinear version of the (linear) auto-correlation and cross-correlation functions, and was developed by Fraser and Swinney (3). Mutual information measures the certainty with which a measurement can be predicted, given the outcome of another related measurement. Examples of the later include the same EEG channel at a different time, and another EEG channel at the same (or different) time. The MIF indicates the average information (in bits) that can be inferred from one measurement about a second measurement, and is a function of the time delay (number of time steps) between the measurements. The mutual information function also measures the nonlinear time dependent correlation in the same signal. For EEG data, information decay in an individual channel (univariate MIF) indicates local time scale, as the average time lag ($t_i-t_j$) that makes $x(t_i)$ independent of $x(t_j)$, and corresponds to the first (local) minimum ($M_1$ in timesteps) in the MIF (3). For use herein, a minimum is defined as two successive decreases in the signal value, followed by two successive increases in signal value. Other definitions were tested and found to yield less consistent results. The MIF, I(Q,S), and system entropy (H) for two measurements (Q and S) are defined by:

$$I(Q, S) = I(S, Q) = H(Q) + H(S) - H(S, Q) \qquad \text{Eq. 13}$$

$$H(S) = -\sum_i P_S(s_i) \log[P_S(s_i)] \qquad \text{Eq. 14}$$

$$H(S, Q) = -\sum_{i,j} P_{SQ}(s_i, q_j) \log[P_{SQ}(s_i, q_j)] \qquad \text{Eq. 15}$$

S denotes the whole system that consists of a set of possible messages (measurements for the value of s), $s_1$, $s_2$, ..., $s_n$, with associated probabilities $P_s(s_1)$, $P_s(s_2)$, ..., $P_s(s_n)$. Q denotes a second system that consists of a set of possible messages (measured values with a time delay relative to the $s_i$ values), $q_1$, $q_2$, ..., $q_n$ with associated probabilities $P_Q(q_1)$, $P_Q(q_2)$, ..., $P_Q(q_n)$. The function $P_{SQ}(s_i, q_j)$ denotes the joint probability of both states occurring simultaneously. If the logarithm is taken to the base two, then H is in units of bits. Fraser and Swinney (3) describe the details for evaluating I(Q,S), including a sequence of recursive partitions in ($s_i$, $q_j$,) space to achieve adequate accuracy with tailoring to the local data structure.

The maximum-likelihood correlation dimension (D) is based on the early work by Takens (14) with modifications for noise (13):

$$D = \left[\left(-\frac{1}{M}\right) \sum_{i,j} \ln\left(\frac{r_{ij} - r_n}{1 - r_n}\right)\right]^{-1} \qquad \text{Eq. 16}$$

where M is the number of randomly sampled point pairs, $r_{ij}$ is the normalized maximum-norm distance between the (randomly chosen) i–j point pairs as defined in Eq. 17 (below), and $r_n$ is the normalized distance (scale length) associated with noise as measured from the time serial data. The distances are normalized with respect to some nominal scale length ($L_0$), i.e. $r_{ij}=L_{ij}/L_0$ and $r_n=L_n/L_0$ with $L_0$ as a representative scale length (typically a multiple of the absolute average deviation). The choice of scale length is a balance between a small scale for sensitivity to local dynamics (typically at $L_0 < 5a$) and avoidance of excessive noise (typically at $L_0 \geq a$). The distances ($L_{ij}$) are defined by:

$$L_{ij} = \max_{0 \leq k \leq m-1} |x_{i+k} - x_{j+k}| \qquad \text{Eq. 17}$$

where m is the average number of points per cycle from Eq. 12 (i.e., m=$T_c$). Schouten et al. (40) describe the details for evaluating Eqs 16–17 to measure of the number of degrees of freedom in a system (e.g., the number of coupled first-order differential equations to depict the dynamics).

The Kolmogorov entropy (K-entropy or simply entropy) measures the rate of information loss per unit time, or (alternatively) the degree of predictability. A positive, finite entropy generally is considered to be a clear demonstration that the time series and its underlying dynamics are chaotic. An infinite entropy indicates a stochastic, non-deterministic (totally unpredictable) phenomenon. For entropy determination, one begins with two orbits on a chaotic attractor that are initially very close together. The entropy then is estimated from the average divergence time for pairs of initially-close orbits. More precisely, the entropy is obtained from the average time for two points on an attractor to go from an initial separation ($L<L_0$), to become separated by more than a specific distance ($L \geq L_0$). The maximum-likelihood entropy (K) is:

$$K = -f_s \log\left(1 - \frac{1}{\underline{b}}\right) \quad \text{Eq. 18}$$

and $$\underline{b} = \left(\frac{1}{M}\right) \sum_{i=1}^{M} b_i \quad \text{Eq. 19}$$

with $b_i$ as the number of timesteps for two points, initially within $L<L_0$, to diverge to $L \geq L_0$. The work by Schouten et al. (12), and references therein, provide details of the method. Note that the entropy used here is the order-2 Kolmogorov entropy which hereafter is called simply entropy.

The entropy (K) and correlation dimension (D) usually are reported in the limit of zero scale length. However, EEG data (and all biomedical data) have substantial noise. Consequently, the nonlinear measures, K and D, are reported for a finite scale length ($L_0$) that is slightly larger than the noise. Thus, the values of K and D, that are reported here, do not capture the full complexity of brain dynamics, i.e., their values are smaller than expected for the zero-scale-length limit. K and D are interpreted as nonlinear statistical indices of finite-scale dynamic structure.

EXAMPLE I

The method and apparatus of this invention are illustrated by the analysis of two datasets. Both datasets are from the same patient, who is a 20-year-old female with a lifelong history of seizures, beginning at age 4 months. The cause of the seizures is not established, although neuro-imaging studies (including computerized tomography and magnetic resonance) are normal. The seizures are poorly controlled despite treatment with various combinations of anti-epileptic drugs, which at the time of the recordings were Phenytoin, Phenobarbital, and Felbamate. The seizures are partial complex with some occasions of secondary generalization. During the seizure designated Example I, the patient was sitting up in bed, doing some neurophysiologic testing. Her EEG shows an activated pattern. She then showed automatisms with picking movements and staring, followed by vocalizations (several seconds of screams). Hyper-extended head and neck posturing followed. Her upper extremities became flexed, and then she showed clonic activity, involving abduction/adduction at the shoulders and hips. There was tonic posturing and clonic activity of all extremities. The convulsive movements were associated with high-amplitude EEG waves, involving spikes, polyspikes, and much artifact activity. As the clinical seizure spontaneously terminated, the subject was unresponsive and made loud snoring sounds. Then, the brain wave amplitudes became quite suppressed. The automatisms were associated with polyspike discharges from the left frontal region. After seizure termination, spike discharges occurred from this same region, followed by suppressed background waves.

The results from Example I involved four analyses (e-, f-, g-, and h-data) on the three epochs of channel 13 data (epileptic seizure and post-seizure, non-seizure, and transition from non-seizure to seizure). These three epochs of data were provided and analyzed as three separate, non-contiguous ten-minute data segments. The non-seizure data segment ended several hours before the transition data, which in turn ended ~10 seconds before the start of the seizure data segment. The results are combined as one thirty-minute set of plots for the e-data (FIG. 4), f-data (FIG. 5), g-data (FIG. 6), and h-data (FIG. 7), with gaps in the analysis to indicate where one dataset ends and the next dataset begins. In particular, the data from 10–590s is the non-seizure epoch with large amplitude signals at 520–600s from chewing and drinking. The data from 610–1190s is the (transition) period immediately before seizure. The data from 1210–1790s includes the seizure and post-ictal phases. The various measures were obtained for every analysis-window, and the resulting values were plotted at the center of the 20-second analysis-window.

Each plot in FIGS. 4–7 for Example I displays the analysis-window-centered measure as a solid line. The dashed line (- - -) in each figure is the average value of the measure (from Eq. 6) over an 11-point averaging-window, plotted at the central (sixth) point of the averaging window. The dotted line (. . .) in each figure is the corresponding sample standard deviation over this 11-point averaging-window (from Eq. 9), also plotted at the central point of the averaging-window. The scale length ($L_0$) was fixed at ~1.4 times the absolute average deviation, as obtained by averaging over the complete non-seizure e-data, and was used in all the analyses as the reference scale length for all three data epochs. Smaller values for this scale length caused numerical problems in the determinations of the correlation dimension and the K-entropy; larger values limited the resolution of the nonlinear measures.

The clinical seizure in Example I occurred from 53 to 95s in the (third) seizure epoch (1253 to 1295s in FIGS. 4–7). Rhythmic convulsions began at 1295s, and post-ictal features appeared at 1314s.

Trends in the average and standard deviation (SD) of each measure for this dataset are very different during the transition dataset (610–1190s) as compared to the non-seizure dataset (10–590s). The following notation is used for the subsequent discussion: The average of each measure is denoted by an under-barred symbol (e.g., the average entropy as $\underline{K}$; and the average correlation dimension as $\underline{D}$). The SD of each measure (x) is denoted by $\sigma_X$ (e.g., the SD of the entropy as $\sigma_K$; and the SD of the correlation dimension as $\sigma_D$).

The linear and nonlinear measures for Example I have much variability, but clear distinctions exist between the non-seizure and transition results, clearly distinguishable as trends useful as seizure predictors for this patient. One such trend is that the SD in the skewedness ($\sigma_S$) of f-data is $\geq 0.5$ for 440s during transition (690–1130s), but remains at this level for only 200s during the non-seizure period (60–260s). This same trend occurs in the e-data for 380s during transition (750–1130s), compared to 165s during the non-seizure period (80–245s). Thus, the continuous occurrence of ($\sigma_S \geq 0.5$ for >200s may be an indicator of an impending seizure for this patient.

A second trend in the transition data of Example I (but not in the non-seizure data) is a regular sequence of quasi-periodic maximum and minima in $\underline{K}$ and $\underline{D}$ of e-data at 710s (max), 805s (min), 900s (max), 980s (min), and 1070s (max). The first four times are coincident with minima and maxima in $\underline{T}_c$ of e-data at 710s (min), 805s (max), 900s (min), and 980s (max). This trend also occurs in $\underline{K}$ and $\underline{D}$ of g-data at 690s (max), 790s (min), 880s (max), 965s (min), and 1060s (max), with corresponding minima and maxima in $\underline{T}_c$, for the first four times. This trend occurs again in $\underline{K}$ and $\underline{D}$ of h-data at 695s (max), 790s (min), 870s (max), 960s (min), and 1060s (max), with corresponding minima and maxima in $\underline{T}_c$ that approximate the first four times. The times at which the extrema occur is within ±10s among to e-/g-/h-data, and is consistent with uncertainty that is inherent in the 10s overlap of successive analysis windows.

A third trend in the g-data of Example I involves a valley in $\underline{M}_1$ that is coincident with a peak in $\sigma_M$. The rise in $\sigma_M$ begins at 785s, peaking at 885s, with the subsequent decrease ending at 990s. The corresponding times for $\underline{M}_1$ (i.e., beginning of the fall, minimum, and end of the rise) are coincident with the corresponding time values for $\sigma_M$. This trend in $\underline{M}_1$ and $\sigma_M$ corresponds to oscillations in $M_1$ that increase in amplitude from 785–885s and subsequently decay from 885–990s. Note that the extrema in $\underline{M}_1$ and $\sigma_M$ occur at 885s, which is approximately coincident with one of the extrema times in ($\underline{K}$, $\underline{D},\underline{T}_c$) as discussed in the previous paragraph.

Other trends are inferred in Example I from the total variation in the average and in the standard deviation of each measure during the non-seizure period relative to that during the transition period. For example, the average skewedness in e-data (see FIG. 4) is $-0.52 \leq s \leq 0.25$ (during the non-seizure period) and $-0.51 \leq s \leq 0.24$ (during transition). The resulting total variations ($\Delta$) in average are $\Delta_n=0.77$ (with the subscript "n" denoting non-seizure) and $\Delta_t=0.75$ (with the subscript "t" denoting transition). The ratio of these variations is $\Delta_t/\Delta_n=0.97$. Likewise, the total variation in the SD of the skewedness of e-data is $\Delta\sigma_n=0.9$ (non-seizure) and $\Delta\sigma_t=0.6$ (transition). Then, the ratio of the total variation in standard deviation is $\Delta\sigma_t/\Delta\sigma_n=0.67$. Table 1 summarizes these comparisons between non-seizure and transition data, taken from FIGS. 4–7. Most of these variations are not significant because noise in the EEG data (and biological data in general) makes comparisons tenuous for ratios near unity. However, starred values (*) in Table 1 are probably significant, corresponding to substantial ratios (e.g. >2 or <0.5). We note that some small ratios ($\leq 0.1$) exist only for the linear measures of g-data (e.g., $\Delta_t/\Delta_n=0.016$ and $\Delta\sigma_t/\Delta\sigma_n=0.082$ for kurtosis, and $\Delta\sigma_t/\Delta\sigma_n=0.11$ for skewedness). In this patient, these variations mean that the non-seizure EEG is much more variable than the transition EEG for g-data for this type of seizure, and the transition is detectable with linear and non-linear statistics.

Listed below are indicators of transition from non-seizure to seizure found in Example I:

$\sigma_s \geq 0.5$ for >200 sec. for e-data and f-data quasi-periodic min/max in $\underline{K}$ of e-data, g-data, and h-data quasi-periodic min/max in $\underline{D}$ of e-data, g-data, and h-data quasi-periodic min/max in $\underline{T}_c$ of e-data, g-data, and h-data valley in $\underline{M}_1$ coincident with peak in $\sigma_m$ of g-data $\Delta_t/\Delta_n \leq 0.5$ for g-data (skewedness)

$\Delta\sigma_t/\Delta\sigma_n < 0.5$ for f-data and g-data (skewedness)

$\Delta_t/\Delta_n \leq 0.5$ for e-data, g-data, and h-data (kurtosis)

$\Delta\sigma_t/\Delta\sigma_n < 0.5$ for e-data, g-data, and h-data (kurtosis)

$\Delta_t/\Delta_n < 0.5$ for g-data ($T_c$)

$\Delta\sigma_t/\Delta\sigma_n < 0.5$ for g-data and h-data ($T_c$)

$\Delta\sigma_t/\Delta\sigma_n < 0.5$ for f-data and h-data (K)

$\Delta_t/\Delta_n < 0.5$ for f-data ($M_1$)

$\Delta\sigma_t/\Delta\sigma_n < 0.5$ for f-data ($M_1$)

$\Delta_t/\Delta_n < 0.5$ for g-data (D)

TABLE 1

Ratios of averages and standard deviations for Example I

| Specific measure | e-data | f-data | g-data | h-data |
|---|---|---|---|---|
| skewedness (s) | | | | |
| $\Delta_t/\Delta_n$ | 0.97 | 1.1 | 0.29* | 0.77 |
| $\Delta\sigma_t/\Delta\sigma_n$ | 0.67 | 0.48* | 0.11* | 0.73 |
| kurtosis (k) | | | | |
| $\Delta_t/\Delta_n$ | 0.37* | 0.90 | 0.016* | 0.44* |
| $\Delta\sigma_t/\Delta\sigma_n$ | 0.28* | 0.58 | 0.082* | 0.42* |
| Time per cycle ($T_c$) | | | | |
| $\Delta_t/\Delta_n$ | 0.51 | 0.67 | 0.35* | 0.63 |
| $\Delta\sigma_t/\Delta\sigma_n$ | 0.67 | 0.62 | 0.35* | 0.46* |
| Entropy (K) | | | | |
| $\Delta_t/\Delta_n$ | 0.71 | 0.50 | 0.70 | 0.53 |
| $\Delta\sigma_t/\Delta\sigma_n$ | 0.93 | 0.33* | 0.82 | 0.42* |
| 1$^{st}$ Min. in MIF ($M_1$) | | | | |
| $\Delta_t/\Delta_n$ | 1.3 | 0.40* | 0.52 | 0.67 |
| $\Delta\sigma_t/\Delta\sigma_n$ | 0.51 | 0.40* | 0.91 | 0.50 |
| Correlation dimensions (D) | | | | |
| $\Delta_t/\Delta_n$ | 0.56 | 0.73 | 0.39* | 0.97 |
| $\Delta\sigma_t/\Delta\sigma_n$ | 0.64 | 0.57 | 0.50 | 0.78 |

EXAMPLE II

The dataset designated Example II is from the same patient as Example I, who is a 20-year-old female with a lifelong history of seizures as previously described in Example I. During the seizure designated Example II, the patient is lying in bed, awake with her right upper extremity in a flexed posture. The EEG shows spike-wave discharges in the left hemisphere, after which the brain waves become very sharp, dominated by high frequency activity and artifacts. The patient showed eye deviation to the right and some head turning to the right, with head jerking also to the right, but without any usual posturing of the right upper extremity. The eye/head turning is preceded by a high-frequency vocalization. After the clinical seizure spontaneously terminated, the EEG shows high amplitude wave slowing and subsequent amplitude suppression. The subject remained awake during the seizure but was poorly responsive.

The results from Example II for channel 13 involved four analyses (e-, f-, g-, and h-data) on one 23-minute dataset that included all three epochs of channel 13 data (epileptic seizure, non-seizure, and transition from non-seizure to seizure). The non-seizure period spanned 10–400s. The transition period occurred over 410–1200s. The seizure began at 1245s and ended at 1290s. The patient was aphasic at 1300s, with head movements and verbalization at 1315s.

The scale length ($L_0$) was fixed at ~1.0 times the absolute average deviation, as obtained by averaging over the non-seizure e-data, and was used in all the analyses as the reference scale length for all three data epochs. The results were obtained as before, and are plotted for e-data (FIG. 8), f-data, (FIG. 9), g-data (FIG. 10), and h-data (FIG. 11).

As in Example I, certain trends in the data are useful as seizure predictors for this patient. One such trend in Example II involves the sample standard deviation of the correlation dimension ($\sigma_D$) for e-h data. In particular, $\sigma_D$ has a small variation during the non-seizure period, but undergoes large rises and falls during transition. Moreover, $\sigma_D$ has minimal variation (($\sigma D \leq 0.1$) for 30–150s intervals during transition. This trend is unique to the transition period.

A second trend in Example II involves the entropy (K) for f- and h-data. In these cases, K has a large, aperiodic variations during transition, and substantially less variation during the non-seizure period. Also during transition, the entropy becomes very small (K<0.00005) for several intervals that have a duration of 10–100s.

A third trend in Example II occurs in the first minimum of the MIF ($M_1$). From 700–1100s, $\underline{M}_1$ in the e-data gradually decreases below a nominal critical value (40 in this example) to a minimum of 21 just before the seizure. A similar decrease occurs in $\underline{M}_1$ from 400–1100s in g-data, to a minimum of 17. Two cycles of a quasi-periodic variation of $\underline{M}_1$ in f-data appear from 400–800s, with a valley-to-valley period of 200s.

A fourth trend in Example II involves the entropy (K) for e-data. From 600–730s, the average entropy ($\underline{K}$) increases monotonically, while K undergoes oscillations of decreasing amplitude about $\underline{K}$. The entropy then decreases abruptly (K=0.045→K=0.0004) during 760–820s. Then, $\underline{K}$ again increases monotonically over 850–920s, while K undergoes oscillations of increasing amplitude about this average. The entropy then decreases abruptly (K=0.018→K=0.001) during 930–970s. The previous cycle is repeated over 1000–1100s (increasing $\underline{K}$ with K undergoing oscillations of increasing amplitude), followed by a smaller decrease in (K=0.009→K=0.003). This last decrease is difficult to distinguish from the imbedded oscillations, which subsequently rise again as part of the seizure.

Other trends in the average and standard deviation of each measure for Example II are very different during the transition period (410–1200s) as compared to the non-seizure period (10–400s). Table 2 shows the ratios of the variations in the average and in the standard deviation of each measure during the non-seizure period with that during the transition period. As before, most of these variations are not significant because noise in the EEG data makes comparisons tenuous for ratios near unity. However, starred values (*) in Table 2 are probably significant, corresponding to substantial ratios (e.g. >2 or <0.5). Note that some large ratios (>10) occur for the linear measures in Table 2. These large ratios mean that the transition data is much more variable for this seizure than for the non-seizure data.

Listed below are indicators of transition from non-seizure to seizure found in Example II: $(\sigma_D)_n$ has small variation, $(\sigma_D)_t$ has large variation (e-data, f-data, g-data, and h-data) $(K)_t$ has large variation, $(K)_n$ has much less variation (f-data and h-data)
$(K)_t$ becomes very small (<5×10$^{-5}$) for 10–100s
gradual decrease in $\underline{M}_1$ (e-data and g-data)
quasi-periodic variation in $M_1$ (f-data)
$\underline{K}$ increases monotonically while K oscillates about $\underline{K}$ (e-data), followed by an abrupt decrease in $\underline{K}$
$\Delta_t/\Delta_n > 2$ for SD of e-data, f-data, g-data, and h-data
$\Delta\sigma_t/\Delta\sigma_n > 2$ for SD of e-data, f-data, and h-data
$\Delta_t/\Delta_n > 2$ for AAD of e-data, f-data, g-data, and h-data
$\Delta\sigma_t/\Delta\sigma_n > 2$ for AAD of e-data, f-data, and h-data
$\Delta_t/\Delta_n > 2$ for skewedness of e-data, f-data, g-data, and h-data
$\Delta\sigma_t/\Delta\sigma_n > 2$ for skewedness of e-data, f-data, g-data, and h-data
$\Delta_t/\Delta_n > 2$ for kurtosis of e-data, f-data, g-data, and h-data
$\Delta\sigma_t/\Delta\sigma_n > 2$ for kurtosis of e-data, f-data, g-data, and h-data
$\Delta\sigma_t/\Delta\sigma_n < 0.5$ for K of g-data
$\Delta_t/\Delta_n > 2$ for M, of f-data, g-data, and h-data
$\Delta_t/\Delta_n > 2$ for D of h-data
$\Delta_t/\Delta_n > 2$ for D of e-data and h-data.

TABLE 2

Ratios of averages and standard deviations for Example II

| Specific measure | e-data | f-data | g-data | h-data |
|---|---|---|---|---|
| std. deviation ($\sigma$) | | | | |
| $\Delta_t/\Delta_n$ | 3.9* | 4.8* | 2.1* | 3.3* |
| $\Delta\sigma_t/\Delta\sigma_n$ | 15.7* | 25.9* | 1.2 | 6.5* |
| abs. avg. dev. (a) | | | | |
| $\Delta_t/\Delta_n$ | 2.5* | 2.9* | 2.3* | 3.0* |
| $\Delta\sigma_t/\Delta\sigma_n$ | 10.6* | 12.7* | 1.1 | 3.6* |
| skewedness (s) | | | | |
| $\Delta_t/\Delta_n$ | 4.8* | 4.1* | 8.6* | 5.5* |
| $\Delta\sigma_t/\Delta\sigma_n$ | 3.1* | 3.8* | 44.5* | 23.9* |
| kurtosis (k) | | | | |
| $\Delta_t/\Delta_n$ | 6.9* | 8.6* | 10.8* | 17.5* |
| $\Delta\sigma_t/\Delta\sigma_n$ | 11.7* | 6.9* | 36.1* | 54.2* |
| Time per cycle ($T_c$) | | | | |
| $\Delta_t/\Delta_n$ | 1.4 | 1.3 | 1.8 | 1.0 |
| $\Delta\sigma_t/\Delta\sigma_n$ | 1.2 | 1.8 | 1.0 | 0.67 |
| Entropy (K) | | | | |
| $\Delta_t/\Delta_n$ | 1.5 | 1.9 | 1.00 | 2.0 |
| $\Delta\sigma_t/\Delta\sigma_n$ | 0.99 | 1.5 | 0.49* | 1.6 |
| 1$^{st}$ Min. in MIF ($M_1$) | | | | |
| $\Delta_t/\Delta_n$ | 1.5 | 3.0* | 2.6* | 3.5* |
| $\Delta\sigma_t/\Delta\sigma_n$ | 1.4 | 1.1 | 1.7 | 2.0 |
| Correlation dimension (D) | | | | |
| $\Delta_t/\Delta_n$ | 1.8 | 1.8 | 1.7 | 3.3* |
| $\Delta\sigma_t/\Delta\sigma_n$ | 4.3* | 1.9 | 1.7 | 2.2* |

It has been shown by the foregoing that certain trends such as sudden increases, sudden decreases, peaks, and valleys and combinations thereof in time serial sequences of nonlinear measures hereinbefore described are seizure predictors.

By comparing indicative trends in non-linear measures of the patient's brain wave data with known seizure indicators, it can be clearly determined whether the indicative trends correspond with known seizure predictors whether a seizure is oncoming in the patient.

Tables 1 and 2 and FIGS. 4–11 clearly indicate that epileptic seizures are indicated by a number of trends in nonlinear measures of brain-wave data including the following:

a a long-time, large value of the standard deviation of the skewedness of e-data 101;
b a long-time, large value of the standard deviation of the skewedness off-data 103;
c quasi-periodic maxima and minima in the average entropy of e-data 105;
d quasi-periodic maxima and minima in the average entropy of g-data 107;
e quasi-periodic maxima and minima in the average entropy of h-data 109;
f quasi-periodic maxima and minima in the average correlation dimension of e-data 111;
g quasi-periodic maxima and minima in the average correlation dimension of g-data 113;
h quasi-periodic maxima and minima in the average correlation dimension of h-data 115;
i quasi-periodic maxima and minima in the average number of time steps per cycle of e-data 117;

j quasi-periodic maxima and minima in the average number of time steps per cycle of g-data 119;

k quasi-periodic maxima and minima in the average number of time steps per cycle of h-data 121;

l coincidence of the minima and maxima selected from the group consisting of items c) through k) of this list and combinations thereof;

m a valley in the average of the minimum in the mutual information function in g-data 122;

n a peak in the standard deviation of the minimum in the mutual information function in g-data 123;

o coincidence of the extrema selected from the group consisting of items m) and n) of this list and combinations thereof with at least one of extrema times selected from the group consisting of items c) through k) of this list and combinations thereof;

p large decreases and increases in the standard deviation of the correlation dimension of e-data 125;

q large decreases and increases in the standard deviation of the correlation dimension of f-data 127;

r large decreases and increases in the standard deviation of the correlation dimension of g-data 129;

s large decreases and increases in the standard deviation of the correlation dimension of h-data 131;

t large, aperiodic variations in entropy of f-data, including some values close to zero for >10 seconds 133;

u large, aperiodic variations in entropy of h-data, including some values close to zero for >10 seconds 135;

v the average of the first minimum of the mutual information function of e-data gradually decreases below a critical value 137;

w the average of the first minimum of the mutual information function of g-data gradually decreases below a critical value 139;

x quasi-periodic maxima and minima in the average of the first minimum of the mutual information function of f-data 141;

y aperiodic maxima and minima in the average entropy of e-data 143;

z oscillations in entropy of e-data of increasing or decreasing magnitude, about the average entropy of item y 145;

aa small variation ratio in average skewedness ($\Delta_t/\Delta_n$) of g-data 147;

ab small variation ratio in standard deviation ($\Delta\sigma_t/\Delta\sigma_n$) of skewedness of f-data 149;

ac small variation ratio in standard deviation ($\Delta\sigma_t/\Delta\sigma_n$) of skewedness of g-data 151;

ad small variation ratio in average kurtosis ($\Delta_t/\Delta_n$) of e-data 153;

ae small variation ratio in average kurtosis ($\Delta_t/\Delta_n$) of g-data 155;

af small variation ratio in average kurtosis ($\Delta_t/\Delta_n$) of h-data 157;

ag small variation ratio in standard deviation ($\Delta\sigma_t/\Delta\sigma_n$) of kurtosis of e-data 159;

ah small variation ratio in standard deviation ($\Delta\sigma_t/\Delta\sigma_n$) of kurtosis of g-data 161;

ai small variation ratio in standard deviation ($\Delta\sigma_t/\Delta\sigma_n$) of kurtosis of h-data 163;

aj small variation ratio in average number of timesteps per cycle ($\Delta_t/\Delta_n$) of g-data 165;

ak small variation ratio in standard deviation ($\Delta\sigma_t/\Delta\sigma_n$) of number of timesteps per cycle of g-data 167;

al small variation ratio in standard deviation ($\Delta\sigma_t/\Delta\sigma_n$) of number of timesteps per cycle of h-data 169;

am small variation ratio in standard deviation ($\Delta\sigma_t/\Delta\sigma_n$) of entropy of f-data 171;

an small variation ratio in standard deviation ($\Delta\sigma_t/\Delta\sigma_n$) of entropy of h-data 173;

ao small variation ratio in the average of the first minimum in mutual information function ($\Delta_t/\Delta_n$) of f-data 175;

ap small variation ratio in standard deviation ($\Delta\sigma_t/\Delta\sigma_n$) of first minimum in mutual information function of f-data 177;

aq small variation ratio in average correlation dimension ($\Delta_t/\Delta_n$) of g-data 179;

ar large variation ratio in average ($\Delta_t/\Delta_n$) of the standard deviation of e-data 181;

as large variation ratio in average ($\Delta_t/\Delta_n$) of the standard deviation of f-data 183;

at large variation ratio in average ($\Delta_t/\Delta_n$) of the standard deviation of g-data 185;

au large variation ratio in average ($\Delta_t/\Delta_n$) of the standard deviation of h-data 187;

av large variation ratio in standard deviation ($\Delta\sigma_t/\Delta\sigma_n$) of the standard deviation of e-data 189;

aw large variation ratio in standard deviation ($\Delta\sigma_t/\Delta\sigma_n$) of the standard deviation of f-data 191;

ax large variation ratio in standard deviation ($\Delta\sigma_t/\Delta\sigma_n$) of the standard deviation of h-data 193;

ay large variation ratio in the average of the absolute average deviation ($\Delta_t/\Delta_n$) of e-data 195;

az large variation ratio in the average of the absolute average deviation ($\Delta_t/\Delta_n$) of f-data 197;

ba large variation ratio in the average of the absolute average deviation ($\Delta_t/\Delta_n$) of g-data 199;

bb large variation ratio in the average of the absolute average deviation ($\Delta_t/\Delta_n$) of h-data 201;

bc large variation ratio in the standard deviation of the absolute average deviation ($\Delta\sigma_t/\Delta\sigma_n$) of e-data 203;

bd large variation ratio in the standard deviation of the absolute average deviation ($\Delta\sigma_t/\Delta\sigma_n$) of f-data 205;

be large variation ratio in the standard deviation of the absolute average deviation ($\Delta\sigma_t/\Delta\sigma_n$) of h-data 207;

bf large variation ratio in average skewedness ($\Delta_t/\Delta_n$) of e-data 209;

bg large variation ratio in average skewedness ($\Delta_t/\Delta_n$) of f-data 211;

bh large variation ratio in average skewedness ($\Delta_t/\Delta_n$) of g-data 213;

bi large variation ratio in average skewedness ($\Delta_t/\Delta_n$) of h-data 215;

bj large variation ratio in standard deviation ($\Delta\sigma_t/\Delta\sigma_n$) of skewedness of e-data 217;

bk large variation ratio in standard deviation ($\Delta\sigma_t/\Delta\sigma_n$) of skewedness of f-data 219;

bl large variation ratio in standard deviation ($\Delta\sigma_t/\Delta\sigma_n$) of skewedness of g-data 221;

bm large variation ratio in standard deviation ($\Delta\sigma_t/\Delta\sigma_n$) of skewedness of h-data 223;

bn large variation ratio in average kurtosis ($\Delta_t/\Delta_n$) of e-data 225;

bo large variation ratio in average kurtosis ($\Delta_t/\Delta_n$) of f-data 227;

bp large variation ratio in average kurtosis ($\Delta_t/\Delta_n$) of g-data 229;

bq large variation ratio in average kurtosis ($\Delta_t/\Delta_n$) of h-data 231;

br large variation ratio in standard deviation ($\Delta\sigma_t/\Delta\sigma_n$) of kurtosis of e-data 233;

bs large variation ratio in standard deviation ($\Delta\sigma_t/\Delta\sigma_n$) of kurtosis of f-data 235;

bt large variation ratio in standard deviation ($\Delta\sigma_t/\Delta\sigma_n$) of kurtosis of g-data 237;

bu large variation ratio in standard deviation ($\Delta\sigma_t/\Delta\sigma_n$) of kurtosis of h-data 239;
bv small variation ratio in standard deviation ($\Delta\sigma_t/\Delta\sigma_n$) of entropy of g-data 241;
bw large variation ratio in the average of the first minimum in mutual information function ($\Delta_t/\Delta_n$) of f-data 243;
bx large variation ratio in the average of the first minimum in mutual information function ($\Delta_t/\Delta_n$) of g-data 245;
by large variation ratio in the average of the first minimum in mutual information function ($\Delta_t/\Delta_n$) of h-data 247;
bz large variation ratio in average correlation dimension ($\Delta_t/\Delta_n$) of h-data 249;
ca large variation ratio in standard deviation ($\Delta\sigma_t/\Delta\sigma_n$) of correlation dimension of e-data 251;
cb large variation ratio in standard deviation ($\Delta\sigma_t/\Delta\sigma_n$) of correlation dimension of h-data 253; and
cc combinations thereof.

While there has been shown and described what are presently considered the preferred embodiments of the invention, it will be obvious to those skilled in the art that various changes and modifications can be made therein without departing from the scope of the inventions defined by the appended claims.

What is claimed is:

1. A method for automatically predicting an epileptic seizure in a patient comprising the steps of:
(a) providing at least one channel of a patient's raw brain wave data, called e-data, selected from the group consisting of electroencephalogram data and magnetoencephalogram data;
(b) separating the e-data into artifact data, called f-data, and artifact-free data, called g-data, while preventing phase distortions in the data;
(c) processing g-data through a low-pass filter to produce a low-pass-filtered version of g-data, called h-data;
(d) applying at least one measure selected from the group consisting of linear statistical measures minimum and maximum, standard deviation, absolute minimum deviation, skewedness, and kurtosis, and nonlinear measures time steps per cycle, Kolmogorov entropy, first minimum in mutual information function, and correlation dimension to at least one type of data selected from the group consisting of e-data, f-data, g-data, and h-data to provide at least one time serial sequence of nonlinear measures, from which at least one indicative trend selected from the group consisting of abrupt increases, abrupt decreases, peaks, valleys, and combinations thereof is determined;
(e) comparing at least one indicative trend with at least one known seizure predictor; and
(f) determining from said comparison whether an epileptic seizure is oncoming in the patient.

2. The method as described in claim 1 wherein said at least one time serial sequence of linear and nonlinear measures is selected from the group consisting of: the standard deviation of the correlation dimension for e-data; the standard deviation of the correlation dimension for f-data; the standard deviation of the correlation dimension for g-data; the standard deviation of the correlation dimension for h-data; the Kolmogorov entropy for f-data; the Kolmogorov entropy for h-data; the first minimum in the Mutual Information Function for e-data; the first minimum in the Mutual Information Function for g-data; the average Kolmogorov entropy for e-data; the skewedness for f-data; the kurtosis for f-data, and combinations thereof.

3. The method as described in claim 1 wherein said at least one seizure predictor is selected from the group consisting of:

(a) a long-time, large value of the standard deviation of the skewedness of e-data;
(b) a long-time, large value of the standard deviation of the skewedness of f-data;
(c) quasi-periodic maxima and minima in the average Kolmogorov entropy of e-data;
(d) quasi-periodic maxima and minima in the average Kolmogorov entropy of g-data;
(e) quasi-periodic maxima and minima in the average Kolmogorov entropy of h-data;
(f) quasi-periodic maxima and minima in the average correlation dimension of e-data;
(g) quasi-periodic maxima and minima in the average correlation dimension of g-data;
(h) quasi-periodic maxima and minima in the average correlation dimension of h-data;
(i) quasi-periodic maxima and minima in the average number of time steps per cycle of e-data;
(j) quasi-periodic maxima and minima in the average number of time steps per cycle of g-data;
(k) quasi-periodic maxima and minima in the average number of time steps per cycle of h-data;
(l) coincidence of the minima and maxima selected from the group consisting of items c through k of this list and combinations thereof;
(m) a valley in the average of the minimum in the mutual information function in g-data;
(n) a peak in the standard deviation of the minimum in the mutual information function in g-data;
(o) coincidence of the extrema selected from the group consisting of items m and n of this list and combinations thereof with at least one of extrema times selected from the group consisting of items c through k of this list and combinations thereof;
(p) large decreases and increases in the standard deviation of the correlation dimension of e-data;
(q) large decreases and increases in the standard deviation of the correlation dimension of f-data;
(r) large decreases and increases in the standard deviation of the correlation dimension of g-data;
(s) large decreases and increases in the standard deviation of the correlation dimension of h-data;
(t) large, aperiodic variations in Kolmogorov entropy of f-data, including some values close to zero for >10 seconds;
(u) large, aperiodic variations in Kolmogorov entropy of h-data, including some values close to zero for >10 seconds;
(v) the average of the first minimum of the mutual information function of e-data gradually decreases below a critical value;
(w) the average of the first minimum of the mutual information function of g-data gradually decreases below a critical value;
(x) quasi-periodic maxima and minima in the average of the first minimum of the mutual information function of f-data;
(y) aperiodic maxima and minima in the average e Kolmogorov entropy of e-data;
(z) oscillations in Kolmogorov entropy of e-data of increasing or decreasing magnitude, about the average Kolmogorov entropy of item y;
(aa) small variation ratio in average skewedness ($\Delta_t/\Delta_n$) of g-data;
(ab) small variation ratio in standard deviation ($\Delta\sigma_t/\Delta\sigma_n$) of skewedness of f-data;
(ac) small variation ratio in standard deviation ($\Delta\sigma_t/\Delta\sigma_n$) of skewedness of g-data;

(ad) small variation ratio in average kurtosis ($\Delta_t/\Delta_n$) of e-data;
(ae) small variation ratio in average kurtosis ($\Delta_t/\Delta_n$) of g-data;
(af) small variation ratio in average kurtosis ($\Delta_t/\Delta_n$) of h-data;
(ag) small variation ratio in standard deviation ($\Delta\sigma_t/\Delta\sigma_n$) of kurtosis of e-data;
(ah) small variation ratio in standard deviation ($\Delta\sigma_t/\Delta\sigma_n$) of kurtosis of g-data;
(ai) small variation ratio in standard deviation ($\Delta\sigma_t/\Delta\sigma_n$) of kurtosis of h-data;
(aj) small variation ratio in average number of timesteps per cycle ($\Delta_t/\Delta_n$) of g-data;
(ak) small variation ratio in standard deviation ($\Delta\sigma_t/\Delta\sigma_n$) of number of timesteps per cycle of g-data;
(al) small variation ratio in standard deviation ($\Delta\sigma_t/\Delta\sigma_n$) of number of timesteps per cycle of h-data;
(am) small variation ratio in standard deviation ($\Delta\sigma_t/\Delta\sigma_n$) of Kolmogorov entropy of f-data;
(an) small variation ratio in standard deviation ($\Delta\sigma_t/\Delta\sigma_n$) of Kolmogorov entropy of h-data;
(ao) small variation ratio in the average of the first minimum in mutual information function ($\Delta_t/\Delta_n$) of f-data;
(ap) small variation ratio in standard deviation ($\Delta\sigma_t/\Delta\sigma_n$) of first minimum in mutual information function of f-data;
(aq) small variation ratio in average correlation dimension ($\Delta_t/\Delta_n$) of g-data;
(ar) large variation ratio in average ($\Delta_t/\Delta_n$) of the standard deviation of e-data;
(as) large variation ratio in average ($\Delta_t/\Delta_n$) of the standard deviation of f-data;
(at) large variation ratio in average ($\Delta_t/\Delta_n$) of the standard deviation of g-data;
(au) large variation ratio in average ($\Delta_t/\Delta_n$) of the standard deviation of h-data;
(av) large variation ratio in standard deviation ($\Delta\sigma_t/\Delta\sigma_n$) of the standard deviation of e-data;
(aw) large variation ratio in standard deviation ($\Delta\sigma_t/\Delta\sigma_n$) of the standard deviation of f-data;
(ax) large variation ratio in standard deviation ($\Delta\sigma_t/\Delta\sigma_n$) of the standard deviation of h-data;
(ay) large variation ratio in the average of the absolute average deviation ($\Delta_t/\Delta_n$) of e-data;
(az) large variation ratio in the average of the absolute average deviation ($\Delta_t/\Delta_n$) of f-data;
(ba) large variation ratio in the average of the absolute average deviation ($\Delta_t/\Delta_n$) of g-data;
(bb) large variation ratio in the average of the absolute average deviation ($\Delta_t/\Delta_n$) of h-data;
(bc) large variation ratio in the standard deviation of the absolute average deviation ($\Delta\sigma_t/\Delta\sigma_n$) of e-data;
(bd) large variation ratio in the standard deviation of the absolute average deviation ($\Delta\sigma_t/\Delta\sigma_n$) of f-data;
(be) large variation ratio in the standard deviation of the absolute average deviation ($\Delta\sigma_t/\Delta\sigma_n$) of h-data;
(bf) large variation ratio in average skewedness ($\Delta_t/\Delta_n$) of e-data;
(bg) large variation ratio in average skewedness ($\Delta_t/\Delta_n$) of f-data;
(bh) large variation ratio in average skewedness ($\Delta_t/\Delta_n$) of g-data;
(bi) large variation ratio in average skewedness ($\Delta_t/\Delta_n$) of h-data;
(bj) large variation ratio in standard deviation ($\Delta\sigma_t/\Delta\sigma_n$) of skewedness of e-data;
(bk) large variation ratio in standard deviation ($\Delta\sigma_t/\Delta\sigma_n$) of skewedness of f-data;
(bl) large variation ratio in standard deviation ($\Delta\sigma_t/\Delta\sigma_n$) of skewedness of g-data;
(bm) large variation ratio in standard deviation ($\Delta\sigma_t/\Delta\sigma_n$) of skewedness of h-data;
(bn) large variation ratio in average kurtosis ($\Delta_t/\Delta_n$) of e-data;
(bo) large variation ratio in average kurtosis ($\Delta_t/\Delta_n$) of f-data;
(bp) large variation ratio in average kurtosis ($\Delta_t/\Delta_n$) of g-data;
(bq) large variation ratio in average kurtosis ($\Delta_t/\Delta_n$) of h-data;
(br) large variation ratio in standard deviation ($\Delta\sigma_t/\Delta\sigma_n$) of kurtosis of e-data;
(bs) large variation ratio in standard deviation ($\Delta\sigma_t/\Delta\sigma_n$) of kurtosis of f-data;
(bt) large variation ratio in standard deviation ($\Delta\sigma_t/\Delta\sigma_n$) of kurtosis of g-data;
(bu) large variation ratio in standard deviation ($\Delta\sigma_t/\Delta\sigma_n$) of kurtosis of h-data;
(bv) small variation ratio in standard deviation ($\Delta\sigma_t/\Delta\sigma_n$) of Kolmogorov entropy of g-data;
(bw) large variation ratio in the average of the first minimum in mutual information function ($\Delta_t/\Delta_n$) of f-data;
(bx) large variation ratio in the average of the first minimum in mutual information function ($\Delta_t/\Delta_n$) of g-data;
(by) large variation ratio in the average of the first minimum in mutual information function ($\Delta_t/\Delta_n$) of h-data;
(bz) large variation ratio in average correlation dimension ($\Delta_t/\Delta_n$) of h-data;
(ca) large variation ratio in standard deviation ($\Delta\sigma_t/\Delta\sigma_n$) of correlation dimension of e-data;
(cb) large variation ratio in standard deviation ($\Delta\sigma_t/\Delta\sigma_n$) of correlation dimension of h-data; and
(cc) combinations thereof.

4. The method as described in claim 1 wherein the artifact data is separated from the raw data by use of a zero-phase filter.

5. The method as described in claim 1 wherein said low-pass filter comprises a standard low-pass filter selected from the group consisting of second-order, third-order and fourth-order low-pass filters at frequencies between about 35 Hz and about 60 hz.

6. The method as described in claim 5 wherein said low-pass filter comprises a standard fourth-order low-pass filter at 50 Hz.

7. Apparatus for automatically predicting an epileptic seizure in a patient comprising:
(a) data provision means for providing at least one channel of raw brain wave data, called e-data, selected from the group consisting of electroencephalogram data and magnetoencephalogram data;
(b) separation means for separating e-data into artifact data, called f-data, and artifact-free data, called g-data, while preventing phase distortions in the data, communicably connected to said data provision means;
(c) low-pass filter means for filtering g-data to produce a low-pass filtered version of g-data, called h-data, communicably connected to said separation means;
(d) application means for applying at least one measure selected from the group of consisting of linear statistical measures minimum and maximum, standard deviation, absolute minimum deviation, skewedness, and kurtosis, and nonlinear measures time steps per cycle, Kolmogorov entropy, first minimum in mutual information function, and correlation dimension to at least one type of data selected from the group consisting of e-data, f-data, g-data, and h-data to provide at least one time serial sequence of nonlinear measures, from which at least one indicative trend selected from the group consisting of abrupt increases, abrupt decreases, peaks, valleys, and combinations thereof is determined, communicably connected to said low-pass filter means;

(e) comparison means for comparing at least one indicative trend with known seizure predictors, connected to said application means; and, (f) determination means for determining from the comparison whether an epileptic seizure is oncoming in the patient, communicably connected to said comparison means.

8. The apparatus as described in claim 7 wherein said at least one time serial sequence of linear and nonlinear measures is selected from the group consisting of: the standard deviation of the correlation dimension for e-data; the standard deviation of the correlation dimension for f-data; the standard deviation of the correlation dimension for g-data; the standard deviation of the correlation dimension for h-data; the Kolmogorov entropy for f-data; the Kolmogorov entropy for h-data; the first minimum in the Mutual Information Function for e-data; the first minimum in the Mutual Information Function for g-data; the average Kolmogorov entropy for e-data; the skewedness for f-data; the kurtosis for f-data, and combinations thereof.

9. The apparatus as described in claim 7 wherein said at least one seizure predictor is selected from the group consisting of:

(a) a long-time, large value of the standard deviation of the skewedness of e-data;

(b) a long-time, large value of the standard deviation of the skewedness of f-data;

(c) quasi-periodic maxima and minima in the average Kolmogorov entropy of e-data;

(d) quasi-periodic maxima and minima in the average Kolmogorov entropy of g-data;

(e) quasi-periodic maxima and minima in the average Kolmogorov entropy of h-data;

(f) quasi-periodic maxima and minima in the average correlation dimension of e-data;

(g) quasi-periodic maxima and minima in the average correlation dimension of g-data;

(h) quasi-periodic maxima and minima in the average correlation dimension of h-data;

(i) quasi-periodic maxima and minima in the average number of time steps per cycle of e-data;

(j) quasi-periodic maxima and minima in the average number of time steps per cycle of g-data;

(k) quasi-periodic maxima and minima in the average number of time steps per cycle of h-data;

(l) coincidence of the minima and maxima selected from the group consisting of items c through k of this list and combinations thereof;

(m) a valley in the average of the minimum in the mutual information function in g-data;

(n) a peak in the standard deviation of the minimum in the mutual information function in g-data;

(o) coincidence of the extrema selected from the group consisting of items m and n of this list and combinations thereof with at least one of extrema times selected from the group consisting of items c through k of this list and combinations thereof;

(p) large decreases and increases in the standard deviation of the correlation dimension of e-data;

(q) large decreases and increases in the standard deviation of the correlation dimension of f-data;

(r) large decreases and increases in the standard deviation of the correlation dimension of g-data;

(s) large decreases and increases in the standard deviation of the correlation dimension of h-data;

(t) large, aperiodic variations in Kolmogorov entropy of f-data, including some values close to zero for >10 seconds;

(u) large, aperiodic variations in Kolmogorov entropy of h-data, including some values close to zero for >10 seconds;

(v) the average of the first minimum of the mutual information function of e-data gradually decreases below a critical value;

(w) the average of the first minimum of the mutual information function of g-data gradually decreases below a critical value;

(x) quasi-periodic maxima and minima in the average of the first minimum of the mutual information function of f-data;

(y) aperiodic maxima and minima in the average Kolmogorov entropy of e-data;

(z) oscillations in Kolmogorov entropy of e-data of increasing or decreasing magnitude, about the average Kolmogorov entropy of item y;

(aa) small variation ratio in average skewedness ($\Delta_t/\Delta_n$) of g-data;

(ab) small variation ratio in standard deviation ($\Delta\sigma_t/\Delta\sigma_n$) of skewedness of f-data;

(ac) small variation ratio in standard deviation ($\Delta\sigma_t/\Delta\sigma_n$) of skewedness of g-data;

(ad) small variation ratio in average kurtosis ($\Delta_t/\Delta_n$) of e-data;

(ae) small variation ratio in average kurtosis ($\Delta_t/\Delta_n$) of g-data;

(af) small variation ratio in average kurtosis ($\Delta_t/\Delta_n$) of h-data;

(ag) small variation ratio in standard deviation ($\Delta\sigma_t/\Delta\sigma_n$) of kurtosis of e-data;

(ah) small variation ratio in standard deviation ($\Delta\sigma_t/\Delta\sigma_n$) of kurtosis of g-data;

(ai) small variation ratio in standard deviation ($\Delta\sigma_t/\Delta\sigma_n$) of kurtosis of h-data;

(aj) small variation ratio in average number of timesteps per cycle ($\Delta_t/\Delta_n$) of g-data;

(ak) small variation ratio in standard deviation ($\Delta\sigma_t/\Delta\sigma_n$) of number of timesteps per cycle of g-data;

(al) small variation ratio in standard deviation ($\Delta\sigma_t/\Delta\sigma_n$) of number of timesteps per cycle of h-data;

(am) small variation ratio in standard deviation ($\Delta\sigma_t/\Delta\sigma_n$) of Kolmogorov entropy of f-data;

(an) small variation ratio in standard deviation ($\Delta\sigma_t/\Delta\sigma_n$) of Kolmogorov entropy of h-data;

(ao) small variation ratio in the average of the first minimum in mutual information function ($\Delta_t/\Delta_n$) of f-data;

(ap) small variation ratio in standard deviation ($\Delta\sigma_t/\Delta\sigma_n$) of first minimum in mutual information function of f-data;

(aq) small variation ratio in average correlation dimension ($\Delta_t/\Delta_n$) of g-data;

(ar) large variation ratio in average ($\Delta_t/\Delta_n$) of the standard deviation of e-data;

(as) large variation ratio in average ($\Delta_t/\Delta_n$) of the standard deviation of f-data;

(at) large variation ratio in average ($\Delta_t/\Delta_n$) of the standard deviation of g-data;

(au) large variation ratio in average ($\Delta_t/\Delta_n$) of the standard deviation of h-data;

(av) large variation ratio in standard deviation ($\Delta\sigma_t/\Delta\sigma_n$) of the standard deviation of e-data;

(aw) large variation ratio in standard deviation ($\Delta\sigma_t/\Delta\sigma_n$) of the standard deviation of f-data;
(ax) large variation ratio in standard deviation ($\Delta\sigma_t/\Delta\sigma_n$) of the standard deviation of h-data;
(ay) large variation ratio in the average of the absolute average deviation ($\Delta_t/\Delta_n$) of e-data;
(az) large variation ratio in the average of the absolute average deviation ($\Delta_t/\Delta_n$) of f-data;
(ba) large variation ratio in the average of the absolute average deviation ($\Delta_t/\Delta_n$) of g-data;
(bb) large variation ratio in the average of the absolute average deviation ($\Delta_t/\Delta_n$) of h-data;
(bc) large variation ratio in the standard deviation of the absolute average deviation ($\Delta\sigma_t/\Delta\sigma_n$) of e-data;
(bd) large variation ratio in the standard deviation of the absolute average deviation ($\Delta\sigma_t/\Delta\sigma_n$) of f-data;
(be) large variation ratio in the standard deviation of the absolute average deviation ($\Delta\sigma_t/\Delta\sigma_n$) of h-data;
(bf) large variation ratio in average skewedness ($\Delta_t/\Delta_n$) of e-data;
(bg) large variation ratio in average skewedness ($\Delta_t/\Delta_n$) of f-data;
(bh) large variation ratio in average skewedness ($\Delta_t/\Delta_n$) of g-data;
(bi) large variation ratio in average skewedness ($\Delta_t/\Delta_n$) of h-data;
(bj) large variation ratio in standard deviation ($\Delta\sigma_t/\Delta\sigma_n$) of skewedness of e-data;
(bk) large variation ratio in standard deviation ($\Delta\sigma_t/\Delta\sigma_n$) of skewedness of f-data;
(bl) large variation ratio in standard deviation ($\Delta\sigma_t/\Delta\sigma_n$) of skewedness of g-data;
(bm) large variation ratio in standard deviation ($\Delta\sigma_t/\Delta\sigma_n$) of skewedness of h-data;
(bn) large variation ratio in average kurtosis ($\Delta_t/\Delta_n$) of e-data;
(bo) large variation ratio in average kurtosis ($\Delta_t/\Delta_n$) of f-data;
(bp) large variation ratio in average kurtosis ($\Delta_t/\Delta_n$) of g-data;
(bq) large variation ratio in average kurtosis ($\Delta_t/\Delta_n$) of h-data;
(br) large variation ratio in standard deviation ($\Delta\sigma_t/\Delta\sigma_n$) of kurtosis of e-data;
(bs) large variation ratio in standard deviation ($\Delta\sigma_t/\Delta\sigma_n$) of kurtosis of f-data;
(bt) large variation ratio in standard deviation ($\Delta\sigma_t/\Delta\sigma_n$) of kurtosis of g-data;
(bu) large variation ratio in standard deviation ($\Delta\sigma_t/\Delta\sigma_n$) of kurtosis of h-data;
(bv) small variation ratio in standard deviation ($\Delta\sigma_t/\Delta\sigma_n$) of Kolmogorov entropy of g-data;
(bw) large variation ratio in the average of the first minimum in mutual information function ($\Delta_t/\Delta_n$) of f-data;
(bx) large variation ratio in the average of the first minimum in mutual information function ($\Delta_t/\Delta_n$) of g-data;
(by) large variation ratio in the average of the first minimum in mutual information function ($\Delta_t/\Delta_n$) of h-data;
(bz) large variation ratio in average correlation dimension ($\Delta_t/\Delta_n$) of h-data;
(ca) large variation ratio in standard deviation ($\Delta\sigma_t/\Delta\sigma_n$) of correlation dimension of e-data;
(cb) large variation ratio in standard deviation ($\Delta\sigma_t/\Delta\sigma_n$) of correlation dimension of h-data; and
(cc) combinations thereof.

10. The apparatus as described in claim 7 wherein said separation means comprises a zero-phase filter.

11. The apparatus as described in claim 10 wherein said zero-phase filter is embodied in a programmed integrated-circuit semiconductor chip.

12. The apparatus as described in claim 7 wherein said low-pass filter means comprises a standard low-pass filter selected from the group consisting of second-order, third-order, and fourth-order low-pass filters at frequencies between about 35 Hz and about 60 Hz.

13. The apparatus as described in claim 7 wherein said low-pass filter comprises a standard fourth-order low-pass filter at about 50 Hz.

14. The apparatus as described in claim 7 further comprising notification means for providing notification that a seizure is oncoming in the patient, the notification means being communicably connected to said determination means.

* * * * *